US009066857B2

(12) United States Patent
Stang

(10) Patent No.: US 9,066,857 B2
(45) Date of Patent: Jun. 30, 2015

(54) DECONTAMINANT EDIBLE PRODUCT, METHODS OF PRODUCTION AND USES THEREOF

(75) Inventor: Michael A. Stang, Baltimore, MD (US)

(73) Assignee: DENOVO INC., Baltimore, MD (US)

( * ) Notice: Subject to any disclaimer, the term of this patent is extended or adjusted under 35 U.S.C. 154(b) by 0 days.

(21) Appl. No.: 12/827,679

(22) Filed: Jun. 30, 2010

(65) Prior Publication Data

US 2011/0244018 A1 Oct. 6, 2011

Related U.S. Application Data

(63) Continuation of application No. 11/604,275, filed on Nov. 27, 2006, now abandoned, which is a continuation-in-part of application No. PCT/US2005/018802, filed on May 27, 2005.

(60) Provisional application No. 60/574,676, filed on May 27, 2004.

(51) Int. Cl.
*A61K 9/00* (2006.01)
*A23L 1/015* (2006.01)
*A23L 1/236* (2006.01)
*A23L 1/30* (2006.01)
*A61K 33/44* (2006.01)
*A61K 9/20* (2006.01)

(52) U.S. Cl.
CPC ............ *A61K 9/0056* (2013.01); *A23L 1/0156* (2013.01); *A23L 1/2362* (2013.01); *A23L 1/30* (2013.01); *A61K 9/2018* (2013.01); *A61K 9/2063* (2013.01); *A61K 9/2086* (2013.01); *A61K 33/44* (2013.01)

(58) Field of Classification Search
CPC ................................................... A23L 1/0156
See application file for complete search history.

(56) References Cited

U.S. PATENT DOCUMENTS

| 4,320,151 A * | 3/1982 | Cole ............................... 426/18 |
| 5,795,586 A | 8/1998 | Stang et al. |
| 6,248,375 B1 * | 6/2001 | Gilles et al. ...................... 426/72 |
| 6,294,189 B1 | 9/2001 | Stang et al. |
| 2001/0000231 A1 * | 4/2001 | Fotos et al. ................... 426/548 |

FOREIGN PATENT DOCUMENTS

| JP | H05-505104 | 12/1994 |
| JP | 2002-524569 | 3/2000 |
| WO | WO98/03260 | 5/1989 |
| WO | WO 00/56175 | * 9/2000 .............. A23L 1/236 |

OTHER PUBLICATIONS

Manley D. Technology of Biscuits, Crackers, and Cookies, 3rd ed. 2000; Woodhead Publishing Limited (p. 295 provided).*
In the Japanese language, Japanese Official Action issued by the Japanese Patent Office on Aug. 23, 2011 in corresponding Japanese Patent Application No. 2007-515403.
International Search Report issued on Mar. 30, 2007 in International Application No. PCT/US2005/018802.
Non-Final Office Action issued on Jun. 8, 2010 in U.S. Appl. No. 11/604,275.
Restriction Requirement issued on Jan. 15, 2010 in U.S. Appl. No. 11/604,275.

* cited by examiner

*Primary Examiner* — Paul Zarek
(74) *Attorney, Agent, or Firm* — Fanelli Haag PLLC

(57) ABSTRACT

The invention relates to an edible product containing a decontaminant. Particularly, the invention relates to an edible product, for instance, a food-like product, containing an effective amount of activated charcoal to mitigate, substantially reduce or cause the cessation of at least one adverse effect associated with the ingestion of a toxic substance. The invention also relates to methods for manufacturing such a decontaminant edible product and uses thereof.

15 Claims, 8 Drawing Sheets

DECONTAMINANT EDIBLE PRODUCT, METHODS OF PRODUCTION AND USES THEREOF

1. CROSS-REFERENCE TO RELATED APPLICATIONS

This application is a continuation of U.S. application Ser. No. 11/604,275, filed Nov. 27, 2006, which is a continuation-in-part of PCT International Application Number PCT/US2005/018802, which was filed May 27, 2005, which claims the benefit of U.S. provisional application No. 60/574,676, filed May 27, 2004, each of which is incorporated herein by reference in its entirety.

2. FIELD OF THE INVENTION

The invention relates to an edible product containing a decontaminant. Particularly, the invention relates to an edible product, for example, a food-like product containing an effective amount of activated charcoal to mitigate, substantially reduce or cause the cessation of adverse effects associated with the ingestion of a toxic substance. The invention also relates to methods for manufacturing such a decontaminant edible product, for example, a food-like product and uses thereof.

3. BACKGROUND OF THE INVENTION

The ingestion of toxic substances has historically been and continues to be a significant problem. While efforts in recent years to mitigate ingestion of toxic substances have arisen, such as conspicuous labeling, tamper-proof sealing, and limiting the number of tablets in bottles of children's medicines, a significant numbers of poisoning incidents continue to occur. Moreover, an overwhelming percentage of these incidents occur in the residence, and the majority of the victims tend to be young children.

In the emergency treatment of poisoning, unless a specific antidote exists, which is uncommon, the effort centers on two main objectives: (i) general support and stabilization and (ii) decontamination. As decontamination and treatment must begin immediately in such toxicological emergencies, often without the benefit of full and thorough clinical information on the patient, it is particularly important that any drug or therapeutic substance administered to the patient be substantially free of adverse effects. Sorbents, which when introduced into the patient's gastrointestinal tract resist decomposition and adsorb the ingested toxins until eventual excretion by the patient, have been employed for decontamination. Of those sorbents, activated charcoal has emerged as the decontaminant of choice. Its administration to poisoning victims has now surpassed the administration of syrup of ipecac as the single most important general toxicological treatment measure.

Activated charcoal is a fine, black, powdery substance which is tasteless, odorless, and non-toxic. Activated charcoal is generally formed by oxidation (activation) of combustion residue derived from a controlled process performed on wood, peat, or other organic material producing a substance composed of extremely porous particles with extraordinarily high internal surface area, typically ranging between about 900 $m^2$/g and about 2000 $m^2$/g. Activated charcoal exhibits great adsorptivity and thus has proven to be quite effective as a decontaminant when introduced in sufficient quantities in a timely manner into the gastrointestinal tract of a poisoning victim. The chief mechanism of action of activated charcoal is by its direct binding with toxins in the gastrointestinal tract. A secondary mechanism, called intestinal dialysis, occurs when activated charcoal in the intestine is able to remove toxins from blood within the intestinal blood vessels. Toxins bound to the activated charcoal in the gastrointestinal tract are excreted in the stool.

Activated charcoal is currently available in several forms to be orally administered to individuals who have ingested a toxin. In the most widely used form, activated charcoal is contained in a suspension such as commercially available ACTIDOSE AQUA and CHARCOAID 2000. Activated charcoal is also available extensively in Europe and to a more limited extent in the United States simply in its powdered or granulated form for mixture within a drinkable liquid prior to ingestion. In yet another form, activated charcoal is contained in tablets or capsules for the treatment of gas and upset stomach. Use of these tablets or capsules for decontamination in toxicological treatment however is not readily feasible due to the large number that would be required and the impracticality of administration to children.

In whatever form activated charcoal is delivered to the gastrointestinal tract (e.g., suspended in a liquid, compressed within a tablet or capsule), the activated charcoal is likely to have beneficial effects if the necessary amount can be expeditiously delivered to the gastrointestinal tract of the victim. Therein lies the single greatest obstacle to optimal utilization of activated charcoal as a decontaminant in toxicological treatment. Except for the tablet or capsule form, which presents its own obstacles to ingestion, the antidotal substances are extremely unpalatable. Liquid antidotal suspensions of activated charcoal, for instance, form a black gritty liquid bearing a striking resemblance to old engine crank case oil, which is off-putting to children and adults alike.

Whereas to an adult poisoning victim, the noxiousness of an activated charcoal-containing antidote may simply represent an unpleasant consequence that must be tolerated to avoid the far greater consequences of the poisoning, it would hardly be such a trivial matter to a young child victim. Children will simply refuse activated charcoal in a form that is not appealing to them.

Aspiration is the most serious risk of activated charcoal administration and, although rare, can be life-threatening. It usually occurs in the patient who is vomiting, is uncooperative, or has altered mental status and is most often associated with the placement of a nasogastric or orogastric tube in the absence of airway protection.

In cases where activated charcoal must be administered to an uncooperative patient, there is no choice but to introduce it through a nasogastric or orogastric tube. This procedure often requires physically restraining the patient. It also carries the risk of trauma to the mouth, pharynx, esophagus and stomach. Inadvertent placement into the tracheo-bronchial tree can result not only in trauma to these areas, but in massive charcoal aspiration which can be fatal.

Efforts have been made to render the currently available forms of activated charcoal more palatable, but those efforts have at best yielded only products that may be somewhat less noxious but certainly not palatable especially to young children. Those efforts at times have led to the introduction of substances or components, which may actually diminish the adsorptivity of the activated charcoal, thereby undermining the singular central function of the antidote.

There is a continued need for an antidotal product containing ample quantities of activated charcoal, which is palatable and in which the adsorptivity of the activated charcoal is not diminished in any substantial measure. In addition, the product should be familiar in form and taste to a young child.

4. SUMMARY OF THE INVENTION

The invention encompasses an edible, toxin-decontaminant product that comprises a therapeutically or prophylactically effective amount of activated charcoal, which is useful in mitigating, substantially reducing, or causing the cessation of at least one adverse effect in a subject that ingested a toxic or poisonous substance or ingested a substance causing illness.

In one embodiment, the invention encompasses an edible, toxin-decontaminant product comprising a plurality of ingredients, which comprises activated charcoal, wherein the ingredients are processed to substantially remove water, for example, by heat to produce the product.

In another embodiment, the invention encompasses an edible, toxin-decontaminant product comprising activated charcoal and comprising one or more flavoring agents, wherein the ingredients are processed to substantially remove water, for example, by heat to produce the product.

In another embodiment, the invention encompasses an edible, toxin-decontaminant product comprising activated charcoal and comprising one or more complexing or thickening agents, wherein the ingredients are processed to substantially remove water, for example, by heat to produce the product.

In another embodiment, the invention encompasses an edible, toxin-decontaminant product comprising activated charcoal and comprising one or more emulsifying agents, wherein the ingredients are processed to substantially remove water, for example, by heat to produce the product.

In another embodiment, the invention encompasses an edible, toxin-decontaminant product comprising activated charcoal and comprising one or more agents to improve porosity and texture, wherein the ingredients are processed to substantially remove water, for example, by heat to produce the product.

In another embodiment, the invention encompasses an edible, toxin-decontaminant product comprising activated charcoal and comprising water, wherein the ingredients are processed to substantially remove water, for example, by heat to produce the product.

In another embodiment, the invention encompasses an edible, toxin-decontaminant product comprising activated charcoal and a plurality of ingredients optionally comprising one or more flavoring agents; optionally comprising one or more complexing or thickening agents; optionally comprising one or more emulsifying agents; water; optionally comprising ammonia, and optionally comprising an agent to improve porosity and texture, wherein the ingredients are processed to substantially remove water, for example, by heat to produce the product.

In another embodiment, the invention encompasses an edible, toxin-decontaminant product comprising activated charcoal and a plurality of ingredients comprising one or more flavoring agents; one or more complexing or thickening agents; one or more emulsifying agents; water; optionally ammonia, and an agent to improve porosity and texture, wherein the ingredients are processed to substantially remove water, for example, by heat to produce the product.

In another embodiment, the invention encompasses a method of producing an edible, toxin-decontaminant product, which comprises activated charcoal and a plurality of ingredients comprising one or more flavoring agents; one or more complexing or thickening agents; and one or more emulsifying agents; optionally ammonia, adding water to produce a first mixture, for instance, a dough; adding an agent to improve porosity and texture, blending to produce a second mixture; and baking the second mixture to produce the product.

In another embodiment, the invention encompasses a gastrointestinal decontaminant produced by the steps of combining activated charcoal and a plurality of ingredients comprising one or more flavoring agents; one or more complexing or thickening agents; and one or more emulsifying agents; adding water to produce a first mixture, for instance, a dough; adding a porosity or texturing agent, and processing the ingredients to substantially remove water to produce a first product; blending together one or more flavoring agents, lecithin, salt, sugar, and shortening to produce a filling mixture composition; and sandwiching said filling mixture composition between two of said first product.

In yet another embodiment, the invention encompasses an edible, toxin-decontaminant product that contains a therapeutically or prophylactically effective amount of activated charcoal and one or more second active agents, which is useful in mitigating, substantially reducing, or causing the cessation of at least one adverse effect in a subject associated with the ingestion of a toxic or poisonous substance or the ingestion of a substance causing illness.

5. BRIEF DESCRIPTION OF THE DRAWINGS

Figure 7:
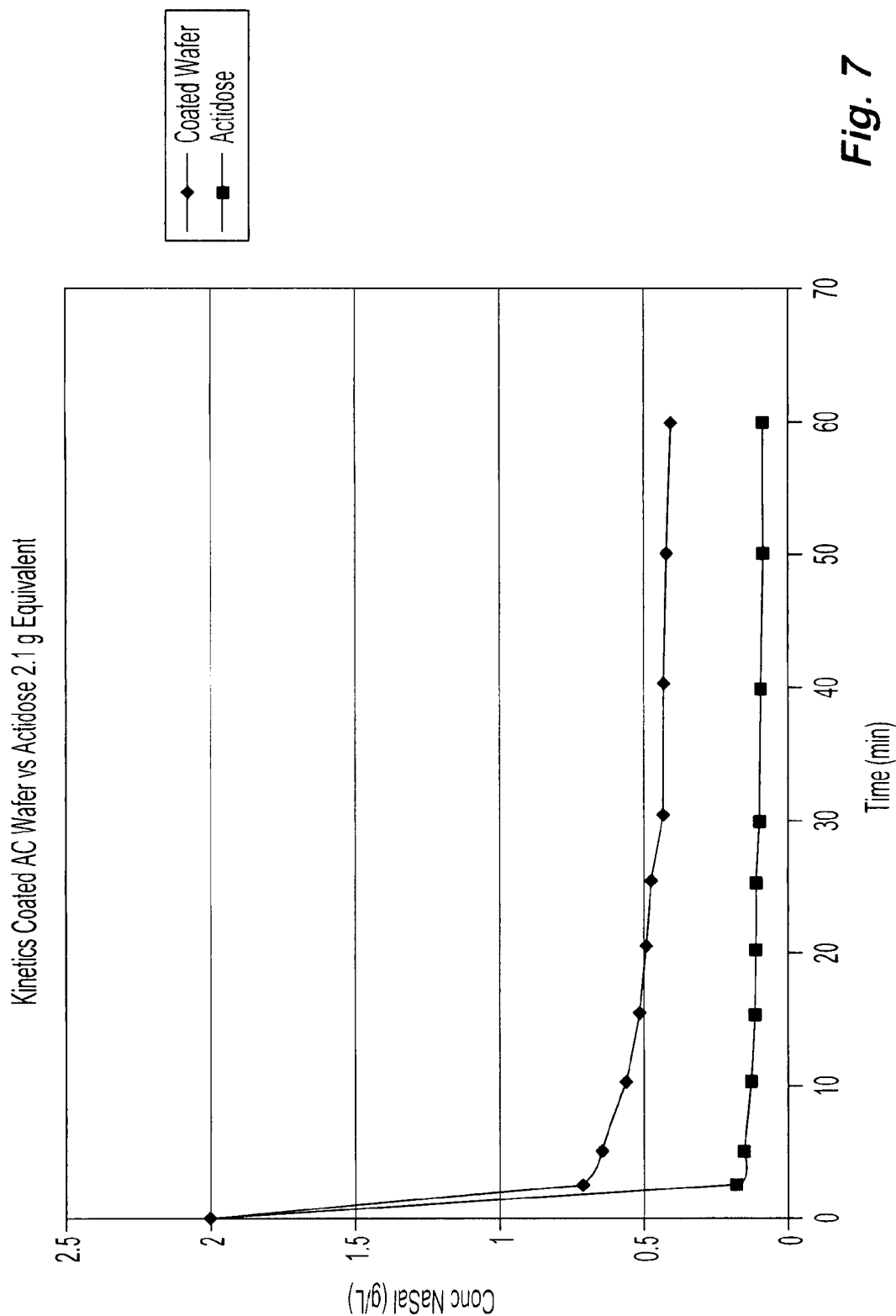
Figure 8:
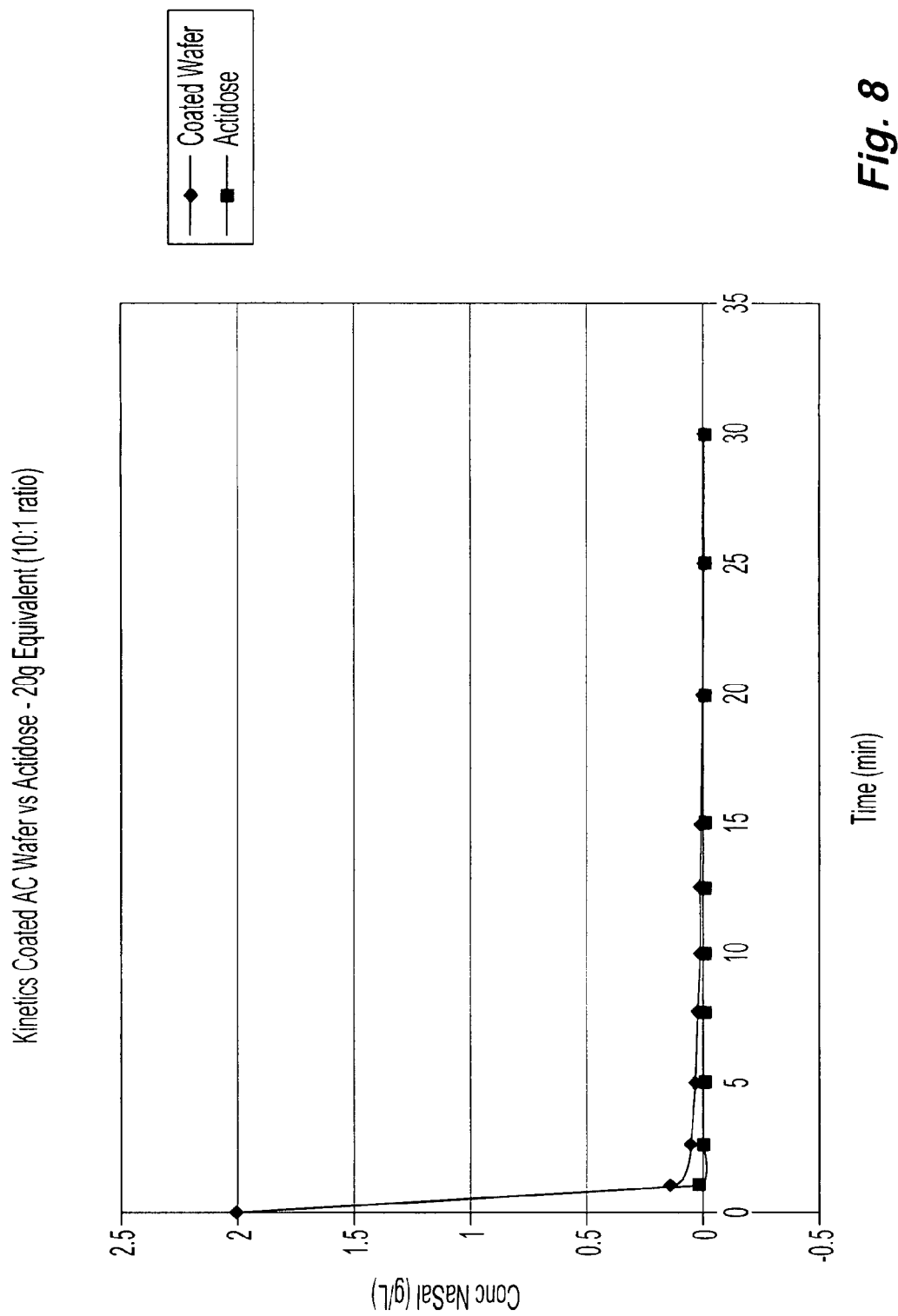

FIG. 7 illustrates the absorption of concentrated sodium salicylate in simulated gastric acid solution by an illustrative activated charcoal edible product containing 2.1 g activated charcoal as compared with ACTIDOSE AQUA containing the same amount of activated charcoal; and FIG. 8 illustrates the absorption of concentrated sodium salicylate in simulated gastric acid solution by an illustrative activated charcoal edible product containing 20 g activated charcoal as compared with ACTIDOSE AQUA containing the same amount of activated charcoal.

6. DETAILED DESCRIPTION OF THE INVENTION 6.1 Definitions

As used herein and unless otherwise indicated, the term "about" will be understood by persons of ordinary skill in the art and will vary to some extent on the context in which the term is used. If there are uses of the term, which are not clear to persons of ordinary skill in the art given the context in which it is used, "about" will mean up to plus or minus 10% of the particular term or amount.

As used herein and unless otherwise indicated, the term "adverse effect(s)" refers to any negative effect on a physiological or physical parameter of a subject. Examples of adverse effects include, but are not limited to, dry mouth, nausea, vomiting, sweating, fever, chills, tremors, or abnormal vital signs, including, but not limited to, for example, increased blood pressure or increased heart rate.

As used herein and unless otherwise indicated, the term "baked" or "baking" refer to placing the combined ingredients that compose the edible product in an oven or other chamber at a defined temperature and allowing the ingredients to produce the product, for instance a food product, for a defined amount of time. The temperature at which the ingredients are "baked" or the "baking" refers to the oven temperature and does not mean heating the actual ingredients to this temperature.

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxy-methyl, pivaloyloxymethyl, and pivaloyloxyethyl esters), lactonyl esters (such as phthalidyl and thiophthalidyl esters), lower alkoxyacyloxyalkyl esters (such as methoxycarbonyloxy-methyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, a amino acid amides, alkoxyacyl amides, and alkylaminoalkyl-carbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "causing the cessation of adverse effects" advantageous partial or complete conclusion or termination of at least one adverse effect associated with the ingestion of a poison or toxin. In an illustrative embodiment, the term "causing the cessation of adverse effects" refers to the partial or complete conclusion or termination of more than one adverse effect associated with the ingestion of a poison or toxin. In a particular illustrative embodiment, the term "causing the cessation of adverse effects" refers to the partial or complete conclusion or termination of all adverse effects associated with the ingestion of a poison or toxin.

As used herein and unless otherwise indicated, the term "coloring agents" are agents that give the edible product a more pleasing appearance, and in addition help the manufacturer to control the product during its preparation and help the user to identify the product. Any of the approved certified water-soluble FD&C dyes, mixtures thereof, or their corresponding lakes may be used. A color lake is the combination by adsorption of a water-soluble dye to a hydrous oxide of a heavy metal, resulting in an insoluble form of the dye. In other embodiments, coloring agents used outside the food industry, for example, pharmaceutical coloring agents, may be used.

As used herein and unless otherwise indicated, the term "complexing agent" and "thickening agent" are used interchangeably and refer to any substance that increases the viscosity of the product. As used herein, these terms included binding agents or binders. Examples of "complexing agents" and "thickening agents" include, but are not limited to, sodium stearoyl lactylate, modified food starch, Inscosity, and high fructose corn syrup. In other embodiments, agents used outside of the food industry for instance pharmaceutical additives, such as PVP, may be used.

As used herein and unless otherwise indicated, the term "dough" refers to a mixture, preferably a thick, soft mixture of one or more materials, preferably dry materials, which may include flour and one or more liquids.

As used herein and unless otherwise indicated, the term "edible product" refers to an edible composition of the invention containing a therapeutically or prophylactically effective amount of activated charcoal and optionally a second active agent or a pharmaceutically acceptable salt, solvate, clathrate, hydrate, or prodrug thereof. Examples of illustrative embodiments of the edible product include, but are not limited to, breads, cakes, muffins, pastries, or cookies containing a therapeutically or prophylactically effective amount of activated charcoal and optionally a second active agent or a pharmaceutically acceptable salt, solvate, clathrate, hydrate, or prodrug thereof.

As used herein and unless otherwise indicated, the term "effective amount" means an amount of activated charcoal or a second active agent or a pharmaceutically acceptable salt, solvate, clathrate, hydrate, or prodrug thereof that is sufficient to provide the desired local or systemic effect and performance at a reasonable benefit/risk ratio attending any medical treatment. Particularly, the term "effective amount" means an amount of activated charcoal or a second active agent or a pharmaceutically acceptable salt, solvate, clathrate, hydrate, or prodrug thereof that is sufficient to mitigate, substantially reduce or cause the cessation of at least one adverse effect associated with the ingestion of a toxic substance, poisonous substance, or an amount of a substance causing illness.

As used herein and unless otherwise indicated, the term "emulsifying agent" refers to a substance having both hydrophilic and hydrophobic character that acts to stabilize an emulsion by coating particles of a dispersed phase and preventing coagulation of colloidal particles. In additional illustrative embodiments, agents used outside of the food industry, for instance, pharmaceutical additives may be used. Examples of "emulsifying agents" include, but are not limited to, monoglycerides and diglycerides. In other embodiments, agents used outside of the food industry for instance pharmaceutical additives may be used.

As used herein and unless otherwise indicated, the term "fat replacer" refers to a substance that attempts to recreate the attributes of fat, while also significantly reducing fat and calorie content. In other embodiments, agents used outside of the food industry, for instance, pharmaceutical additives may be used.

As used herein and unless otherwise indicated, the terms "gastrointestinal decontaminant," and "toxin decontaminant" are used interchangeably and refer to a edible product of the invention containing activated charcoal and optionally a second active agent or a pharmaceutically acceptable salt, solvate, clathrate, hydrate, or prodrug thereof.

As used herein and unless otherwise indicated, the term "herbal ingredient(s)" refers to naturally occurring herbs including, but not limited to, clover, dandelion, saw palmetto, dill, eucalyptus or ginko.

As used herein and unless otherwise indicated, the term "homeopathic ingredient(s)" refers to small doses of medicines, herbs, or both that stimulate a bodily function such as the immune system.

As used herein and unless otherwise indicated, the term "ingestion" refers to oral consumption.

As used herein and unless otherwise indicated, the term "mitigate" or "mitigate adverse effects" are used interchangeably and refer to making less severe, intense, harsh, rigorous, painful or ameliorate at least one adverse effect associated with the ingestion of a toxin, poison or substance causing illness in a subject.

As used herein and unless otherwise indicated the term "neotame" refers to (N-[N-(3,3-dimethylbutyl)-L-a-aspartyl]-L-phenylalanine-1-methyl ester) (i.e., Neotame®).

As used herein and unless otherwise indicated, the term "palatable" and "edible" are used interchangeably and refer to the ability of a subject to orally ingest an edible product of the invention.

As used herein and unless otherwise indicated, the term "pharmaceutical agent" refers to second active agents as set forth in section 5.3 herein. Illustrative examples of "pharmaceutical agents" of the invention include, but are not limited to, antiemetics, antibiotics, antidiarrheals, or antacids.

As used herein and unless otherwise indicated, the term "pharmaceutically acceptable" refers to materials and compositions that are physiologically tolerable and do not typically produce a severe allergic or similar untoward reaction, such as gastric upset, dizziness and the like, when administered to a human. Typically, as used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein and unless otherwise indicated, the term "pharmaceutically acceptable clathrate" means a crystal lattice that contains spaces (e.g., channels) that have a guest molecule (e.g., a solvent or water) trapped within.

As used herein and unless otherwise indicated, the term "pharmaceutically acceptable hydrate" means a stoichiometric or non-stoichiometric amount of water bound by non-covalent intermolecular forces.

As used herein and unless otherwise indicated, the term "pharmaceutically acceptable prodrug" means a derivative of a compound can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise oligonucleotides, peptides, lipids, aliphatic and aromatic groups, or NO, $NO_2$, ONO, and $ONO_2$ moieties. Prodrugs can typically be prepared using well known methods, such as those described in *Burger's Medicinal Chemistry and Drug Discovery*, 172 178, 949 982 (Manfred E. Wolff ed., 5th ed. 1995), and Design of Prodrugs (H. Bundgaard ed., Elsevier, New York 1985).

As used herein and unless otherwise indicated, the phrase "pharmaceutically acceptable salt(s)," includes, but is not limited to, salts of acidic or basic groups. Compounds that are basic in nature are capable of forming a wide variety of salts with various inorganic and organic acids. The acids that may be used to prepare pharmaceutically acceptable acid addition salts of such basic compounds are those that form non-toxic acid addition salts, (i.e., salts containing pharmacologically acceptable anions), including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein and unless otherwise indicated, the term "pharmaceutically acceptable solvate" means a stoichiometric or non-stoichiometric amount of a solvent bound by non-covalent intermolecular forces. Preferred solvents are volatile, non-toxic, and/or acceptable for administration to humans in trace amounts.

As used herein and unless otherwise indicated, the terms "poisonous substance," "poison," "toxin," and "toxic substance" are used interchangeably and refer to a chemical that adversely affects health by causing injury, illness, or death. These terms further include, but are not limited to, any substance, which is harmful to living tissue when ingested orally. Determining factors include concentration, exposure time, particle size, the substance's affinity for tissue and sensitivity of the exposed tissue to that substance. Examples of poisonous substances, poisons, toxins or toxic substances include, but are not limited to, cleaning products (e.g., bleach, detergent, floor cleaner, furniture polish); cosmetics (e.g., nail polish, nail polish remover, make-up), perfumes, plants, pesticides (e.g., bug killers, weed killers, lawn products), prescription or non-prescription drugs.

As used herein and unless otherwise indicated, the term "processed to substantially remove water" refers to any method acceptable in the food industry to remove at least a portion of water, for example to remove from about 10% to about 90%, from about 20% to about 80%, from about 30% to about 70%, from about 40% to about 60% of water in a mixture. In some illustrative embodiments, the processed product will retain or comprise about 2% to about 35% water, about 8% to about 30% water, about 13% to about 25% water, or about 18% to about 22% water. Such methods include, but are not limited to, baking—as defined herein, frying, desiccation (i.e., drying) or any other means available.

As used herein and unless otherwise indicated, the term "prophylactically effective" refers to an amount of activated charcoal capable of mitigating or substantially reducing adverse effects associated with the ingestion of a toxin or poison. In one embodiment, the edible product of the invention is administered as a preventative measure to a subject, preferably a human, who potentially ingested a toxin or poison. Accordingly, the compositions of the invention may be used for the prevention of at least one adverse effect and concurrently treating another (e.g., prevention of adverse effects of poison ingestion while treating emesis or increased heart rate).

As used herein and unless otherwise indicated, the phrase "substance causing illness" refers to any substance that caused a detrimental effect and induces substances that may act in a therapeutic or prophylactic manner in minute levels, but become toxic when the quantity is larger. Examples of substances causing illness include, but are not limited to, nutrients, therapeutic drugs, vitamins, minerals, herbs, prophylactic drugs. Specific examples of substance(s) causing illness include, but are not limited to, St. John's wart, saw palmetto, acetaminophen, aspirin, adriamycin, alcohol, amiodarone, chloramphenical, cisplatin, dapsone, dilantin, disulfiram, glutethimide, hydrazine, isoniazid, vitamin A, vitamin D, vitamin B6, metronidazole, nitrofirantoin, furadantin, macrodantin, penicillin, perhexiline, taxol, vincristine, or zoloft, misomidazole, or lithium.

As used herein, the term "substantially reduces" refers to the ability of an edible product of the invention to measurably reduce the effects of at least one adverse effect associated with ingestion of a toxin or poison. In a preferred embodiment, substantially reduces refers to the ability of a edible product of the invention to reduce all measurable adverse effects associated with ingestion of a toxin or poison.

As used herein, the term "subject" can be a human, a mammal, or an animal. The subject being treated is a patient in need of treatment, preferably a human. In many instances, the subject is a child.

As used herein, the terms "surface area" and "internal surface area" may be used interchangeably.

As used herein and unless otherwise indicated, the term "therapeutically effective" refers to an amount of activated charcoal able to cause an amelioration or substantial reduction of at least one adverse effect associated with the ingestion of a toxin or poison, or at least one discernible symptom thereof. "Therapeutically effective" also refers to an amount of activated charcoal to result in an amelioration of at least one measurable physical parameter, not necessarily discernible by the patient. In yet another embodiment, the term "therapeutically effective" refers to an amount of an activated charcoal to inhibit the progression of at least one adverse effect, either physically (e.g., stabilization of a discernible symptom), physiologically (e.g., stabilization of a physical parameter), or both. In yet another embodiment, the term "therapeutically effective" refers to an amount of activated charcoal resulting in a delayed onset of a disease or disorder. The amount of activated charcoal, which constitutes a "therapeutically effective amount" will vary depending on the toxin or poison ingested, the severity of the condition, and the age and body weight of the subject to be treated, but can be determined routinely by one of ordinary skill in the art having regard to his/her own knowledge and to this disclosure.

6.2 Description

The invention encompasses an edible product, such as a food product, containing a therapeutically or prophylactically effective amount of activated charcoal. In an illustrative embodiment, the edible product is in the form of a snack (e.g., a cookie sandwich or pastry product), which is perceived as palatable, for example, by children. The edible product of the invention generally exhibits the appearance, the texture, the friability, and the sweet flavor, which typically characterize snack products. In a particular embodiment, the edible product is in the form of two wafers sandwiching a cream. However, one of ordinary skill in the art will readily recognize that the edible product of the invention can resemble any dessert product including, but not limited to, a candy product, candy bar, cupcake, cookie, a wafer, a pie, a pastry, a health food bar or a donut. Optionally, the product may have a coating of material including, but not limited to, chocolate or sugar-based glaze. In addition, the product can optionally contain flavor bits or inclusions such as, but not limited to, jimmies, flavor nuggets, cookie pieces, and chocolate chips to enhance flavor, texture, and appearance.

In one embodiment, the invention encompasses an edible, toxin-decontaminant product comprising a plurality of ingredients, which comprises activated charcoal, wherein the ingredients are processed by heat or drying to produce the product.

In another embodiment, the invention encompasses an edible, toxin-decontaminant edible product comprising a plurality of ingredients including one or more of the following: (i) one or more flavoring agents; (ii) one or more complexing or thickening agents; (iii) activated charcoal; (iv) one or more emulsifying agents; (v) water; and (vi) soy protein crisps; wherein the ingredients are processed to substantially remove water, for example, by baking or frying to produce the product. Table 1 discloses approximate weight percents and preferred weight percents of each ingredient after baking the ingredients at a predetermined oven temperature.

TABLE 1

| Ingredient | Approximated Weight %[1] | Preferred Weight %[1] |
|---|---|---|
| Activated Charcoal | 40%-70% | 50% |
| Flavoring Agent | 5%-15% | 9% |
| Complexing/Thickening Agent | 0.5%-4% | 2% |
| Emulsifying Agent | 0.5%-4% | 2% |
| Water | 2%-15% | 5% |
| Porosity/Texture Improving Agent | 5%-15% | 11% |

[1]Weight percentages are determined in the edible product after baking the ingredients.

In an illustrative embodiment, the activated charcoal is characterized by an internal surface area of from about 800 $m^2/g$ to about 3,000 $m^2/g$; in another illustrative embodiment, the activated charcoal is characterized by an internal surface area of from about 1500 $m^2/g$ to about 2,500 $m^2/g$; in yet another illustrative embodiment, the activated charcoal is characterized by an internal surface area of about 2,000 $m^2/g$. However, any ingestable activated charcoal may be used for example the activated charcoal in the product may be in one or more forms such as powder, granules, or brittle chips and can vary in source material, pore size distribution, and adsorptivity. In addition, the product can contain more than one type of activated charcoal.

In another illustrative embodiment, the product includes activated charcoal in an approximate weight range of from about 20% to about 80% thereof. In another illustrative embodiment, the product includes activated charcoal in an approximate weight range of from about 30% to about 70% thereof. In another illustrative embodiment, the product includes activated charcoal in an approximate weight range of from about 45% to about 65% thereof. In another illustrative embodiment, the product includes activated charcoal in an approximate weight of about 60% thereof.

In another embodiment, the flavoring agent is vanilla flavor, chocolate flavor, cocoa, salt, sugar, or a sweetener or combinations thereof; although, any flavoring agent can be used. In an illustrative embodiment, the flavoring agent is in the range of from about 0.001% to about 15%. In a particular illustrative embodiment, the product includes vanilla flavor in the approximating weight range of about 0.01% to about 1% thereof. In yet another illustrative embodiment, the product includes the vanilla flavor in the approximating weight of about 0.05%. In another particular illustrative embodiment, the product includes chocolate flavor in an approximate weight range of about 0.5% to about 3% thereof. In yet another illustrative embodiment, the product includes chocolate flavor in the approximate weight of about 2% thereof. In another particular illustrative embodiment, the product includes salt in an approximate weight range of about 0.1% to about 1% thereof. In an illustrative embodiment, the product includes the salt in the approximating weight of about 0.4% thereof. In another particular illustrative embodiment, the flavoring agent is sweetener in the approximate weight range of about 0.001% to about 10% thereof. In another particular illustrative embodiment, the product includes sweetener in an approximate weight range of about 0.001% to about 5% thereof. In an illustrative embodiment, the product includes a sweetener in the approximate weight of about 2% thereof. In another particular illustrative embodiment, the sweetener present in the product is neotame in the approximate weight range of about 0.001% to about 1.5% thereof. In another particular illustrative embodiment, the product includes sugar in the approximating weight range of about 2% to about 6% thereof. In yet another illustrative embodiment, the product includes the sugar in the approximating weight of about 4.5% thereof. One of ordinary skill in the art will readily understand that the amount of sweetener used is dependent on the specific sweetener. Illustrative examples of sweeteners that can be used in an embodiment of the invention include, but are not limited to, aspartame, sucralose or neotame or mixtures thereof.

In another embodiment, the complexing or thickening agent is sodium stearoyl lactylate or modified food starch or combinations thereof; although, any complexing or thickening agent may be used. In an illustrative embodiment, the product includes the complexing or thickening agent in an approximate weight range of about 0.5% to about 4% thereof. In a particular illustrative embodiment, the product includes sodium stearoyl lactylate in an approximate weight range of about 0.1% to about 2% thereof. In another particular illustrative embodiment, the product includes sodium stearoyl lactylate in the approximate weight of about 0.9% thereof. In another particular illustrative embodiment, the product includes modified food starch in the approximate weight range of about 0.1% to about 2% thereof. In another particular illustrative embodiment, the product includes the modified food starch in the approximate weight of about 0.9% thereof.

In another embodiment, the emulsifying agent is a mono or diglyceride; although or combinations thereof, any emulsifying agent may be used. In an illustrative embodiment, the product includes the emulsifying agent in an approximate weight range of about 0.5% to about 4% thereof. In a particular illustrative embodiment, the product includes an emulsifying agent in the approximate weight range of about 1% to about 3% thereof. In yet another illustrative embodiment, the product includes the emulsifying agent in the approximate weight of about 2% thereof.

In another illustrative embodiment, the product includes water in the approximating weight range of about 15% to about 60% thereof. In a particular illustrative embodiment, the product includes the water in the approximate weight of about 25% thereof.

In another embodiment, the agent to improve porosity and texture is soy protein crisp or another protein product such as a rice protein crisp or is glycerine or combinations thereof. In an illustrative embodiment, the product includes the agent to improve porosity and texture in an approximate weight range of about 5% to about 15% thereof. In a particular illustrative embodiment, the product includes soy protein crisp rice in the approximate weight range of about 5% to about 15% thereof. In another particular illustrative embodiment, the product includes the soy protein crisp rice in the approximate weight of about 11% thereof. In another particular embodiment, the product includes glycerine in the approximate weight range of about 6% to about 8% thereof.

In one embodiment, the baking is done at an oven temperature of from about 250° F. to about 450° F., wherein the combined ingredients are placed in the oven for a time of from about 5 to about 35 minutes. In another embodiment, the combined ingredients are placed in the oven at an oven temperature of about 350° F. for a time of about 5 to about 15 minutes. In yet another embodiment, the baking is done at an oven temperature of about 350° F. for a time of about 10 minutes.

In another embodiment, the invention encompasses a method of producing an edible, toxin-decontaminant product comprising:
   (a) combining a plurality of ingredients including:
      (i) optionally one or more flavoring agents;
      (ii) optionally one or more complexing or thickening agents;
      (iii) activated charcoal; and
      (iv) optionally one or more emulsifying agents;
   (b) blending the components to produce a first mixture;
   (c) optionally adding water to produce a mixture, for instance, a dough;
   (d) optionally adding soy protein crisp rice or rice crisp and blending to produce a second mixture; and
   (e) baking the second mixture to produce the product.

In many embodiments, the instances as described herein may produce a dough.

Table 2 illustrates an illustrative embodiment of the invention with approximate weight percents and preferred weight percents of each ingredient prior to baking.

TABLE 2

| Ingredient | Approximated Weight %[1] | Preferred Weight %[1] |
|---|---|---|
| Activated Charcoal | 20%-70% | 35% |
| Flavoring Agent | 3%-9% | 5% |
| Complexing/Thickening Agent | 0.5%-2% | 1% |
| Emulsifying Agent | 0.5%-2% | 1% |
| Water | 45%-60% | 51% |
| Porosity/Texture Improving Agent | 4%-8% | 7% |

[1]Weight percentages are determined prior to baking the ingredients.

Table 3 illustrates another illustrative embodiment of the invention with approximate weight percents and preferred weight percents of each ingredient prior to baking.

TABLE 3

| Ingredient | Approximated Weight %[1] | Preferred Weight %[1] |
|---|---|---|
| Activated Charcoal | 20%-70% | 24% |
| Flavoring Agent | 0.1%-9% | 1.5% |
| Complexing/Thickening Agent | 0%-40% | 27% |
| Emulsifying Agent | 0%-12% | 7% |
| Water | 15%-60% | 23% |
| Porosity/Texture Improving Agent | 4%-30% | 17% |
| Ammonia | 0%-0.5% | 0.15% |

[1]Weight percentages are determined prior to baking the ingredients.

In an illustrative embodiment, the activated charcoal is characterized by an internal surface area of from about 800 $m^2/g$ to about 3,000 $m^2/g$; in another illustrative embodiment, the activated charcoal is characterized by an internal surface area of from about 1500 $m^2/g$ to about 2,500 $m^2/g$; in yet another illustrative embodiment, the activated charcoal is characterized by an internal surface area of about 2,000 $m^2/g$.

In another illustrative embodiment, the method includes activated charcoal in an approximate weight range of from about 20% to about 80% thereof. In another illustrative embodiment, the method includes activated charcoal in an approximate weight range of from about 25% to about 75% thereof. In another illustrative embodiment, the method includes activated charcoal in an approximate weight range of from about 30% to about 70% thereof.

In another embodiment, the flavoring agent is vanilla flavor, chocolate flavor, salt, sugar, or a sweetener or combinations thereof, although any flavoring agent can be used. In an illustrative embodiment, the method includes vanilla flavor in the approximate weight range of about 0.002% to about 15% thereof. In another illustrative embodiment, the method includes the vanilla flavor in the approximate weight of about 0.01% to about 1%. In yet another illustrative embodiment, the method includes the vanilla flavor in the approximate weight of about 0.05%. In another illustrative embodiment, the method includes chocolate flavor in an approximate weight range of about 0.5% to about 3% thereof. In yet another illustrative embodiment, the method includes chocolate flavor in the approximate weight of about 2% thereof. In an illustrative embodiment, the method includes salt in an approximate weight range of about 0.1% to about 1% thereof. In an illustrative embodiment, the method includes the salt in the approximating weight of about 0.4% thereof. In an illustrative embodiment, the method includes sugar in the approximate weight range of about 2% to about 6% thereof. In yet another illustrative embodiment, the method includes the sugar in the approximate weight of about 4.5%. In an illustrative embodiment, the method includes sweetener in an approximate weight range of about 0.001% to about 10% thereof. In an illustrative embodiment, the method includes a sweetener in the approximate weight of about 2% thereof. One of ordinary skill in the art will readily understand that the amount of sweetener used is dependent on the specific sweetener. Illustrative examples of sweeteners that can be used in an embodiment of the invention include, but are not limited to, aspartame, sucralose or neotame or mixtures thereof.

In another embodiment, the complexing or thickening agent is sodium stearoyl lactylate or modified food starch or combinations thereof; although, any complexing or thickening agent may be used. In an illustrative embodiment, the method includes the complexing or thickening agent in an amount of about 0.5% to about 4%. In an illustrative embodiment, the method includes sodium stearoyl lactylate in an approximate weight range of about 0.1% to about 2% thereof. In yet another illustrative embodiment, the method includes sodium stearoyl lactylate in the approximate weight of about 0.9% thereof. In another illustrative embodiment, the method includes modified food starch in the approximate weight range of about 0.1% to about 2% thereof. In another illustrative embodiment, the method includes the modified food starch in the approximate weight of about 0.9% thereof.

In another embodiment, the emulsifying agent is a mono or diglyceride or combinations thereof; although any emulsifying agent can be used. In an illustrative embodiment, the method includes an emulsifying agent in the approximate weight range of about 0.5% to about 4% thereof. In a particular illustrative embodiment, the method includes an emulsifying agent in the approximate weight range of about 1% to about 3% thereof. In yet another illustrative embodiment, the method includes the emulsifying agent in the approximate weight of about 2% thereof.

In another illustrative embodiment, the method includes water in the approximate weight range of about 15% to about 60% thereof. In another illustrative embodiment, the method includes the water in the approximate weight of about 25% thereof.

In another embodiment, the agent to improve porosity and texture is soy protein crisp or another protein product such as rice crisp or is glycerine or combinations thereof. In an illustrative embodiment, the method includes the agent to improve porosity and texture in an approximate weight range of about 5% to about 15% thereof. In a particular illustrative embodiment, the method includes soy protein crisp rice in the approximate weight range of about 5% to about 15% thereof. In another particular illustrative embodiment, the method includes the soy protein crisp rice in the approximate weight of about 11% thereof. In another particular embodiment, the method includes glycerine in the approximate weight range of about 6% to about 8% thereof.

In one embodiment, the baking is done at an oven temperature of from about 250° F. to about 450° F., wherein the combined ingredients are placed in the oven for a time of from about 5 to about 15 minutes. In another embodiment, the baking is done at an oven temperature of about 350° F. to for a time of about 10 minutes.

In another embodiment, the invention encompasses a gastrointestinal decontaminant produced by the steps of:
(a) combining a plurality of ingredients including:
  (i) optionally one or more flavoring agents;
  (iii) optionally one or more complexing or thickening agents;
  (iii) activated charcoal; and
  (iv) optionally one or more emulsifying agents;
(b) blending the components to produce a mixture;
(c) optionally adding water to produce a mixture, for instance, a dough;
(d) optionally adding an agent to increase texture or porosity to the mixture, and blending;
(e) baking the ingredients to produce a first product;
(f) optionally blending together one or more flavoring agents, lecithin, salt, sugar, and shortening to produce a filling mixture composition; and
(g) sandwiching said filling mixture composition between two of said first product.

In an illustrative embodiment, the activated charcoal is characterized by an internal surface area of from about 800 $m^2/g$ to about 3,000 $m^2/g$; in another illustrative embodiment, the activated charcoal is characterized by an internal surface area of from about 1500 $m^2/g$ to about 2,500 $m^2/g$; in yet another illustrative embodiment, the activated charcoal is characterized by an internal surface area of about 2,000 $m^2/g$.

In another illustrative embodiment, the product includes activated charcoal in an approximate weight range of from about 10% to about 80% thereof. In another illustrative embodiment, the product includes activated charcoal in an approximate weight range of from about 20% to about 60% thereof. In another illustrative embodiment, the product includes activated charcoal in an approximate weight range of from about 25% to about 45% thereof. In a particular illustrative embodiment, the product includes activated charcoal in an approximate weight of about 25% thereof.

In another embodiment, the flavoring agent is vanilla flavor, chocolate flavor, salt, sugar, or a sweetener including, but not limited to, sucrose, glucose, fructose, lactose, acesulfame-K, dextrose, sucralose, saccharin, and aspartame or neotame or combinations thereof. In an illustrative embodiment, the flavoring agent is in the range of from about 0.0001% to about 15%. In a particular illustrative embodiment, the product includes vanilla flavor in the approximate weight range of about 0.01% to about 5% thereof. In yet another illustrative embodiment, the product includes the vanilla flavor in the approximate weight of about 0.05%. In another particular illustrative embodiment, the product includes chocolate flavor in an approximate weight range of about 0.5% to about 3% thereof. In yet another illustrative embodiment, the product includes chocolate flavor in the approximate weight of about 2% thereof. In another illustrative embodiment, the product includes neotame in an amount of about 0.001% to about 1%. In another illustrative embodiment, the product includes neotame in an amount of about 0.002% to about 0.1%. In another particular illustrative embodiment, the product includes salt in an approximate weight range of about 0.1% to about 1% thereof. In an illustrative embodiment, the product includes the salt in the approximate weight of about 0.4% thereof. In another particular illustrative embodiment, the product includes sugar in the approximating weight range of about 2% to about 6% thereof. In yet another illustrative embodiment, the product includes the sugar in the approximate weight of about 4.5% thereof.

In another embodiment, the complexing or thickening agent is sodium stearoyl lactylate, modified food starch, Inscosity, or high fructose corn syrup or combinations thereof. In an illustrative embodiment, the product includes the complexing or thickening agent in an approximate weight range of about 0.5% to about 40% thereof. In a particular illustrative embodiment, the product includes sodium stearoyl lactylate in an approximate weight range of about 5% to about 30% thereof. In another particular illustrative embodiment, the product includes sodium stearoyl lactylate in the approximate weight of about 25% thereof. In another particular illustrative embodiment, the product includes modified food starch in the approximate weight range of about 0.1% to about 2% thereof. In another particular illustrative embodiment, the product includes the modified food starch in the approximate weight range of about 0.9% thereof. In another particular illustrative embodiment, the product includes high fructose corn syrup in the approximate weight range of about 5% to about 40% thereof. In another particular illustrative embodiment, the product includes the high fructose corn syrup in the approximate weight range of about 27% thereof.

In another embodiment, the emulsifying agent is a mono or diglyceride or combinations thereof. Particular examples of emulsifying agents include, but are not limited to, atmul, emplex and lecithin. In an illustrative embodiment, the product includes the emulsifying agent in an approximate weight range of about 0.5% to about 12% thereof. In a particular illustrative embodiment, the product includes an emulsifying agent in the approximate weight range of about 2% to about 9% thereof. In yet another illustrative embodiment, the product includes the emulsifying agent in the approximate weight of about 7% thereof.

In another illustrative embodiment, the product includes water in the approximate weight range of about 15% to about 60% thereof. In a particular illustrative embodiment, the product includes the water in the approximate weight of about 25% thereof.

In another embodiment, the agent to improve porosity and texture is soy protein crisp, rice crisp, or glycerine, or combinations thereof. In an illustrative embodiment, the product includes the agent to improve porosity and texture in an approximate weight range of about 4% to about 30% thereof. In a particular illustrative embodiment, the product includes soy protein crisp in the approximate weight range of about 7% to about 13% thereof. In another particular illustrative embodiment, the product includes the soy protein crisp rice in the approximate weight of about 11% thereof.

In another embodiment, the product optionally contains ammonia in an amount of about 0.5% to about 0.15%. Examples of ammonia suitable for use in the product include, but are not limited to, baker's ammonia, bicarbonate of ammonia, or ammonium bicarbonate or combinations thereof.

In one embodiment, the baking is done at an oven temperature of from about 250° F. to about 450° F., wherein the combined ingredients are placed in the oven for a time of from about 5 to about 15 minutes. In another embodiment, the baking is done at an oven temperature of about 350° F. to for a time of about 10 minutes.

In another embodiment, the invention encompasses a method of producing a toxin-decontaminant product for ingestion into the gastrointestinal tract of a patient comprising:

(a) mixing a plurality of materials including a sweetener, sugar, salt, vanilla flavoring, chocolate flavoring, activated charcoal, modified food starch, monoglycerides and sodium stearoyl lactylate;

(b) adding water to produce a mixture, for instance, a dough and mixing the mixture to produce a mixture of component materials;

(c) adding an agent to improve porosity and texture and blending the composition; and (e) processing to remove water, for example, by baking the mixture at a predetermined temperature for a predetermined time.

In an illustrative embodiment, the activated charcoal is characterized by an internal surface area of from about 800 $m^2/g$ to about 3,000 $m^2/g$; in another illustrative embodiment, the activated charcoal is characterized by an internal surface area of from about 1500 $m^2/g$ to about 2,500 $m^2/g$; in yet another illustrative embodiment, the activated charcoal is characterized by an internal surface area of about 2,000 $m^2/g$.

In another illustrative embodiment, the method includes activated charcoal in an approximate weight range of from about 20% to about 80% thereof. In another illustrative embodiment, the method includes activated charcoal in an approximate weight range of from about 25% to about 75% thereof. In another illustrative embodiment, the method includes activated charcoal in an approximate weight range of from about 30% to about 70% thereof.

In another embodiment, the flavoring agent is vanilla flavor, chocolate flavor, salt, sugar, or a sweetener. In an illustrative embodiment, the method includes vanilla flavor in the approximate weight range of about 0.01% to about 1% thereof. In yet another illustrative embodiment, the product includes the vanilla flavor in the approximate weight of about 0.03%. In another illustrative embodiment, the method includes chocolate flavor in an approximate weight range of about 0.5% to about 2% thereof. In yet another illustrative embodiment, the method includes chocolate flavor in the approximate weight of about 1% thereof. In an illustrative embodiment, the product includes salt in an approximate weight range of about 0.1% to about 1% thereof. In an illustrative embodiment, the method includes the salt in the approximate weight of about 0.1% thereof. In an illustrative embodiment, the method includes sugar in the approximate weight of about 1.5% to about 4% thereof. In yet another illustrative embodiment, the product includes the sugar in the approximate weight of about 2.5% thereof. In an illustrative embodiment, the method includes sweetener in an approximate weight range of about 0.5% to about 2% thereof. In another illustrative embodiment, the method includes a sweetener in an approximate weight range of about 0.001% to about 10% thereof. In an illustrative embodiment, the method includes a sweetener in the approximate weight of about 2% thereof; however, one of ordinary skill in the art will readily understand that the amount of sweetener used is dependent on the specific sweetener. Illustrative examples of sweeteners that can be used in an embodiment of the invention include, but are not limited to, sucrose, glucose, fructose, lactose, acesulfame-K, dextrose, sucralose, saccharin, and aspartame or neotame, or mixtures thereof.

In another embodiment, the complexing or thickening agent is sodium stearoyl lactylate or modified food starch. In an illustrative embodiment, the method includes sodium stearoyl lactylate in an approximate weight range of about 0.1% to about 2% thereof. In yet another illustrative embodiment, the method includes sodium stearoyl lactylate in the approximate weight of about 0.5% thereof. In another illustrative embodiment, the method includes modified food starch in the approximate weight range of about 0.1% to about 2% thereof. In another illustrative embodiment, the method includes the modified food starch in the approximate weight of about 0.5% thereof.

In another embodiment, the emulsifying agent is a mono- or diglyceride. In an illustrative embodiment, the method includes an emulsifying agent in the approximate weight range of about 0.1% to about 2% thereof. In yet another illustrative embodiment, the method includes the emulsifying agent in the approximate weight of about 0.5% thereof.

In another illustrative embodiment, the method includes water in the approximate weight range of about 45% to about 60% thereof. In another illustrative embodiment, the method includes the water in the approximate weight of about 53% thereof.

In another embodiment, the agent to improve porosity and texture is soy protein crisp. In an illustrative embodiment, the method includes soy protein crisp in the approximate weight range of about 4% to about 8% thereof. In another illustrative embodiment, the method includes the soy protein crisp rice in the approximate weight of about 6.6% thereof.

In one embodiment, the baking is done at an oven temperature of from about 250° F. to about 450° F., wherein the combined ingredients are placed in the oven for a time of from about 5 to about 15 minutes. In another embodiment, the baking is done at an oven temperature of about 350° F. to for a time of about 10 minutes.

In yet another embodiment, the invention encompasses a method of producing a toxin-decontaminant product for ingestion into the gastrointestinal tract of a patient comprising: mixing a plurality of materials including a sweetener, sugar, salt, vanilla flavoring, chocolate flavoring, activated charcoal, modified food starch, monoglycerides, and sodium stearoyl lactylate; adding water to produce a mixture, for instance, a dough and mixing said mixture to produce a mixture of component materials; adding soy protein rice crisps and blending the composition; and baking the mixture at a predetermined temperature for a predetermined time.

In another embodiment, the invention encompasses molding, forming or extruding the ingredients using methods known in the art to produce the product in a particular shape or size.

6.2.1 Illustrative Embodiments
6.2.1.1 Wafers Sandwiching a Cream

In one embodiment, the invention encompasses an edible product comprising a pair of biscuit-like wafers and a creamy filling sandwiched therebetween. The wafers may include coloring to make the edible product appealing and easily identified by young children in order to entice them to eat the edible product of the subject invention.

In an illustrative embodiment, a pair of disk-shaped wafers are produced. The wafers exhibit a compressed granular texture and a degree of friability akin to that of a cookie. The degree of friability is such that the wafers are easily crumbled by the average biting force generated by even a very young child. The degree of friability is also such that the crumbled wafers may thereafter be effectively disintegrated by the subsequent chewing action generated by the given young child.

Subject to the allowable ranges of their component composition weight percentages, the wafers exhibit a degree of rich, sweet flavor to accompany their cookie-like crumbly texture, wherein in an illustrative embodiment, the sweet flavor of the wafers is sufficient to encourage substantial chewing prior to ingestion into the user's gastrointestinal tract.

Each wafer includes activated charcoal, in addition to one or more flavoring agents, one or more complexing or thickening agents, one or more emulsifying agents; water, and an agent to improve porosity and texture in the approximate weight range proportions indicated in Table 2.

The combination of activated charcoal, one or more flavoring agents, one or more complexing or thickening agents, one or more emulsifying agents; water, and an agent to improve porosity and texture in the approximate weight range proportions followed by baking the ingredients results in a product having, for example, a cookie-like wafer appearance, which has a consistency emulating that of a baked cookie.

In another embodiment, to further add to the appeal and sweet flavor of the edible product, a cookie is prepared having a cream filling. In such a form, therapeutically or prophylactically effective amounts of activated charcoal are ingested by a subject who has ingested a poison or toxin in an amount sufficient to mitigate, substantially reduce, or cause the cessation of at least one adverse effect associated with the ingestion of the toxin or poison.

In another illustrative embodiment, to enhance the sweet flavor of the wafers, and to enhance the emulation of a cookie treat, a creamy white filling is sandwiched between a pair of wafers. The precise consistency, color, and taste of the filling is not integral to the invention; however, it is preferable that the filling be of a consistency and color appealing to children and that its flavor exhibit a sufficient sweet component to supplement or augment the sweet flavor of the wafers. The pleasant taste further encourages the child to likewise ingest addition "edible product of the invention," which make up the required pharmacological activated charcoal dosage.

An important factor in the proper use of activated charcoal or any other decontaminant in toxicological treatment is, in addition to its ingestion in significant doses by the victim, the promptness with which the ingestion occurs. The edible product of the invention is such that a therapeutically or prophylactically effective amount of activated charcoal is found in the edible product and is ingested with chewing in an ordinary fashion (i.e., the way a subject would chew and swallow any other ingestable food).

In one embodiment, the activated charcoal is administered at the site at which the poisoning incident occurs, which in most cases is the victim's home, immediately following the discovery of the accidental or purposeful ingestion, before the ingested toxins have had the opportunity to be extensively absorbed into the bloodstream.

The edible product produced by the inventive method, given its inherent palatability, could easily be administered in the home or any other setting outside a medical institution, and by any individual. Hence, the edible product of the invention would not only expand the usage of activated charcoal as a decontaminant, but it would actually enhance, in a significant manner, the effectiveness of that usage.

6.2.1.2 Leavening Agents

In the illustrative embodiments set forth above, the ingredients were blended and processed to remove water, for example by baking, in the absence of a leavening agent.

In another illustrative embodiment, the edible product contains a leavening agent to allow the edible product to rise and increase in volume. Embodiments of the invention in the form of a wafer, cracker, or pie crusts can utilize leavening to make them flaky or lighter in texture. Leavening can occur mainly during cooking, such as for pie crusts. In other cases most of the leavening happens prior to baking, as for example with many yeast breads, or more often, leavening may occur partially before and partially when the product is heated. The type of leavening used may depend on the product, for example whether the un-baked product is a batter or a dough.

Several types of leavening agents can be combined to give the maximum amount of lift to the product. For example, a recipe might require sugar and butter to be creamed, representing one type of leavening (i.e., air) and call for baking powder as well, which is another type of leavening (i.e., carbon dioxide).

In addition, the batter or dough should be suitable for holding the expanded shape, before, during, and after cooking. For example a cake containing flour will rise in the oven and hold the volume even after the cake cools and the leavening gases contract. The structure of the cake is strong enough after cooking so that the air cells remain. On the other hand, many cheesecakes and souffles which have little flour will attain a high volume in the oven but will collapse when the product is cooled. The egg protein-based walls of the little air cells are not strong enough to hold up the weight of the cake when the heated air cools and contracts.

6.2.1.3 Cream Filling

The optional cream to be included in an embodiment of the edible product of the invention may be used to enhance the palatability and flavor of the wafers, for example, the cream may improve the texture or mouth feel of the product. In an illustrative embodiment, a creamy white filling is sandwiched between a pair of wafers. The precise consistency, color and taste of the filling is not important to the invention. Thus, the color, texture, and its flavor should supplement or augment the sweet flavor of the wafers themselves.

In one embodiment, the optional cream filling comprises one or more flavoring agents, shortening, lecithin, salt, and sugar. In another embodiment, the optional cream filling is a reduced fat cream filling that comprises sugar, glycerine, shortening, and a fat replacer. In still another embodiment, the optional cream filling is a non-fat cream filling that comprises one or more flavoring agents, lecithin, salt, glycerine, a fat replacer, and one or more emulsifying agents.

In a particular embodiment, the flavoring agent is vanilla or chocolate flavoring. In another particular embodiment, the flavoring is vanilla flavoring. In a particular illustrative embodiment, the flavoring in the optional cream is present in an approximate weight percent of from about 0.05% to about 1%. In another particular illustrative embodiment, the flavoring in the optional cream is in an approximate weight percent of about 0.2%.

In another particular embodiment, the shortening is vegetable cubed shortening. In another particular embodiment, the shortening in the optional cream is present in an approximate weight percent of from about 25% to about 35%. In another particular illustrative embodiment, the shortening in the optional cream is in an approximate weight percent of about 31%.

In another particular embodiment, the lecithin in the optional cream is present in an approximate weight percent of from about 0.01% to about 0.5%. In another particular illustrative embodiment, the lecithin in the optional cream is present in an approximate weight percent of about 0.05%.

In another particular embodiment, the salt in the optional cream is present in an approximate weight percent of from about 0.1% to about 1%. In another particular illustrative embodiment, the salt in the optional cream is present in an approximate weight percent of about 0.25%.

In another particular embodiment, the sugar is powdered sugar. In another particular embodiment, the sugar in the optional cream is present in an approximate weight percent of from about 65% to about 75%. In another particular illustrative embodiment, the sugar in the optional cream is present in an approximate weight percent of about 69%.

In another embodiment, the fat replacer is a carbohydrate-based, protein-based, or non-digestible or non-absorbable fat-based fat replacer. Illustrative examples of fat replacers include, but are not limited to, cellulose, maltodextrins, gums, starches, fiber, polydextrose, and olestra. In another particular embodiment, the fat replacer in the optional cream is present in an approximate weight percent of from about 5% to about 15%. In another particular illustrative embodiment, the fat replacer in the optional cream is present in an approximate weight percent of about 11%.

In an illustrative embodiment, the optional filling is formulated as follows:

| Ingredient | Approximated Weight %[1] | Preferred Weight %[1] |
| --- | --- | --- |
| Sugar | 30%-95% | 65% |
| Glycerine | 10%-50% | 35% |
| Flavoring (*Vanilla* Extract) | 0%-5% | 0.3% |
| Water | 0%-20% | 0% |
| Marshmallow Cream | 0%-70% | 0% |

[1]Weight percentages are determined prior to baking the ingredients.

6.3 Combination Therapy

In certain embodiments of the invention, the edible product of the invention can be used in combination therapy with one or more second active agents. The edible product of the invention and the second active agent may act additively or, more preferably, synergistically. In one embodiment, the edible product comprising activated charcoal is administered concurrently with the administration of the second active agent, which can be part of the edible product.

In another embodiment, the edible product of the invention is administered prior or subsequent to administration of second active agent. The duration of administration of each drug or second active agent can be, for example, several minutes or several hours.

In certain embodiments, when a edible product of the invention is administered concurrently with a second active agent that potentially produces adverse side effects including, but not limited to, toxicity, the therapeutic agent can advantageously be administered at a dose that falls below the threshold at which the adverse side is elicited.

In one illustrative embodiment, the edible products of the invention can be administered together with an antiemetic agent. Antiemetic agents for use in combination with the edible products of the invention include, but are not limited to, cinnarizine, compazine, diphenhydramine, kytril, marinol, meclizine HCl, metoclopramide, promethazine, scopolamine, and zofran.

In another embodiment, the edible products of the invention can be administered together with an antibiotic agent. Antibiotic drugs for use in combination with the edible product of the invention include, but are not limited to, aminoglycosides, streptomycin, neomycin, anamycin, amikacin, gentamicin, tobramycin, streptomycin B, dihydrostreptomycin, spectinomycin, penicillin, ampicillin, hetacillin, amoxicillin, carbenicillin, cephalosporins, cephaloridine, cephalothin sodium, cephaloglycin dihydratem, cephalexin monohydrate, tetracycline, tetracycline hydrochloride, oxytetracycline hydrochloride, chlorotetracycline hydrochloride, doxocycline monohydrate, methacydine hydrochloride, 7-chloro-6-dimethyltetracycline, erythamycin, sulfonamides, carbomycin, oleanodmycin, troleandomycin, polymixin B collistin, and chloramphenicol.

In yet another embodiment, the edible products of the invention can be administered together with an antidiarrheal agent. Antidiarrheal drugs for use in combination with the edible product of the invention include, but are not limited to, loperamide, diphenoxylate, atropine, tincture of opium, paregoric, morphine sulfate, codeine, and methadone.

In another embodiment, the second agent may be a cathartic agent or an agent that induces catharsis. As an example, the second agent may be sorbitol.

In one embodiment the second active agent is administered as a combination with the edible product. In a particular embodiment, the second active agent is baked with the wafer portion of the illustrative edible product described herein. In another particular embodiment, the second active agent is not baked with the wafer portion of the illustrative edible product described herein. In another embodiment, the second active agent is mixed with the cream and then sandwiched between two wafers of the invention.

Without further description, it is believed that one of ordinary skill in the art can, using the preceding description and the following illustrative examples, make and utilize the compounds of the present invention and practice the claimed methods. The following illustrative examples therefore, specifically point out embodiments of the present invention, and are not to be construed as limiting in any way the remainder of the disclosure.

6.4 Therapeutic/Prophylactic Administration and Compositions

The edible products of the invention are administered to achieve efficacious levels of activated charcoal to a subject in need thereof to mitigate, cause the cessation of, or substantially reduce adverse effects associated with the ingestion of a toxin or poison. Thus, the edible product of the invention may be administered orally and chewed to allow the activated charcoal to achieve a therapeutic or prophylactic surface area. A therapeutic or prophylactic surface area is typically achieved by ordinary chewing and swallowing.

Due to the activity of the edible product of the invention, it is useful in veterinary and human medicine. As described above, the edible product of the invention is useful in mitigating, causing the cessation, or substantially reducing adverse effects associated with the ingestion of a toxin or poison.

The invention provides methods of treatment and prophylaxis by administration to a patient a therapeutically effective amount of activated charcoal comprised in an edible product of the invention. The subject may be an animal, including, but not limited, to an animal such a cow, horse, sheep, pig, chicken, turkey, quail, cat, dog, mouse, rat, rabbit, guinea pig, etc., and is more preferably a mammal, and most preferably a human. In some instances, the patient is a child.

The compositions of the invention are intended to be administered orally and may be administered together with another biologically active agent. (See, e.g., section 5.4.1 below). Administration can be at any time after ingestion of a toxin or poison, preferably within about 1 to about 3 hours and more preferably within about 1 hour and most preferably immediately after ingestion of a toxin or poison.

In an illustrative embodiments, it is desirable to administer the edible product of the invention locally to the gastrointestinal tract of the subject. This may be achieved, for example, and not by way of limitation, by oral administration.

The present compositions will contain a therapeutically effective amount of activated charcoal, optionally with an additional therapeutic, preferably in purified form, wherein the additional therapeutic is in a suitable amount of a pharmaceutically acceptable vehicle so as to provide the form for proper administration to the patient.

The term "vehicle" refers to a diluent, adjuvant, excipient, or carrier with which a composition of the invention is administered.

In an illustrative embodiment, the second active agents of the invention are formulated in accordance with routine procedures as a pharmaceutical composition adapted for intravenous administration to human beings. Generally, the ingredients are supplied either separately or mixed together in unit dosage form, for example, as a dry lyophilized powder or water free concentrate in a hermetically sealed container such as an ampoule or sachette indicating the quantity of active agent. Where the composition of the invention is to be administered by intravenous infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

The edible product of the invention for oral delivery can also contain one or more optional agents, for example, pharmaceutical additives such as, PVP; sweetening agents such as fructose, aspartame or saccharin; flavoring agents such as peppermint, oil of wintergreen, saccharine, aspartame, neotame, or cherry; coloring agents; and preserving agents, to provide a pharmaceutically palatable preparation that do not interfere with the preparation of the edible product. In another embodiment, products of the invention may comprise additional coatings or frostings. For example, products of the invention may be enclosed in a chocolate coating as a single wafer or a filled cookie or sandwich cookie. The coating may also decrease the friable nature of the product and increase product stability or shelf life.

The amount of the decontaminant edible product of the invention that will be effective in the treatment or prevention of ingestion of a particular toxin or poison will depend on the nature of the toxin or poison, and can be readily determined by clinicians. In one embodiment, the edible product of the invention is such that it can be administered by a parent or non-clinician, wherein such parent or non-clinician suspects that a child or animal ingested a poison or toxin.

The precise dose to be employed in the compositions will also depend on the seriousness of the toxicity or poisoning, and should be decided according to the judgment of the practitioner and each patient's circumstances. However, the edible product of the invention is such that it can be administered to a subject suspected of ingesting a poison or toxin as one or more individual units and without worry of any adverse effect associated with administration of the edible product provided it is used appropriately.

6.4.1 Oral Administration

The oral formulations of the invention may contain inert ingredients, which allow for protection against the stomach environment, and release of the biologically active material in the intestine. Such formulations, or enteric coatings, are well known in the art. For example, tablets containing a fusion protein in admixture with non-toxic pharmaceutically acceptable excipients, which are suitable for manufacture of tablets, may be used. These excipients may be inert diluents, such as calcium carbonate, sodium carbonate, lactose, calcium phosphate or sodium phosphate; granulating and disintegrating agents, for example, maize starch, gelatin or acacia, and lubricating agents, for example, magnesium stearate, stearic acid, or talc.

The therapeutically or prophylactically effective amount of edible product may be measured in a numbers of ways, including calculated to alleviate symptoms associated with a specific toxin or poison in a subject, such as the symptoms of poison or toxin ingestion.

6.5 Package Containing Edible Product

In a further embodiment, the invention provides a package containing products of the invention. The package will typically comprise a label. Suitable packages include, for example, boxes, cellophane containers or wraps and the like. The package may be formed from a variety of materials such as cellophane or plastic. The package holds the edible product that includes activated carbon in a therapeutically or prophylactically effective amount to mitigate, cause the cessation, or substantially reduce at least one adverse effect associated with the ingestion of a poison or toxin. In addition, the edible product in the package may contain a second active agent. The label on the container typically indicates that the edible product is used for a specific therapy, and may also indicate directions for in vivo use, such as those described above.

Without further description, it is believed that a person of ordinary skill in the art can, using the preceding description and the following working examples, make and utilize the invention and practice the claimed methods. For example, a skilled artisan would readily be able to determine the administration of the edible product of the present invention. The following working examples therefore, specifically point out the illustrative embodiments of the invention, and are not to be construed as limiting in any way the remainder of the disclosure.

7. EXAMPLES

7.1 In Vitro Testing

A rapid test method based on Trinder's Reagent was used in order to determine adsorptivity of the activated charcoal cookie formulation. Tests were conducted in vitro by mixing a predetermined amount of a test substance into a stock solution. The in vitro stock solution used in each test consisted of 1 g/L of sodium salicylate dissolved in a simulated gastric fluid solution containing 2.0 g/L of NaCl, 7.0 mL/L of 12 N strength concentrated HCl and distilled water. The simulated gastric fluid was characterized in this form by a pH level of 1.2, the salicylate of this pH level being more than 99.99% in the form of undissociated salicylic acid, which is very similar in its properties to aspirin, or acetylsalicylic acid.

Equilibrium adsorption tests for determining the total amount of salicylate that a given test substance may potentially adsorb, if allowed to attain equilibrium conditions, was conducted with the following procedures. First, a predetermined amount of the substance to be tested was placed in a glass vial, and 20 mL of the stock solution was added to that vial. The vial was thereafter continuously shaken by placement on a shaking table for approximately 15 hours. This caused the test substance to fully disintegrate such that the activated charcoal contained therein attained virtually perfect adsorption equilibrium with the salicylate in the stock solution.

Kinetic tests were conducted generally by performing the following steps. Approximately 500 mL of the stock solution was poured into a 1 liter glass container. A predetermined quantity of the given test substance was then introduced into the solution in the glass container. The container was then placed on a shaking table and shaken thereby at a 60 cycles per minute oscillation frequency. Samples were taken at various times. Activated charcoal was filtered from each sample and the solution analyzed calorimetrically to determine the salicylic concentration corresponding to the given sample time.

Figure 3:
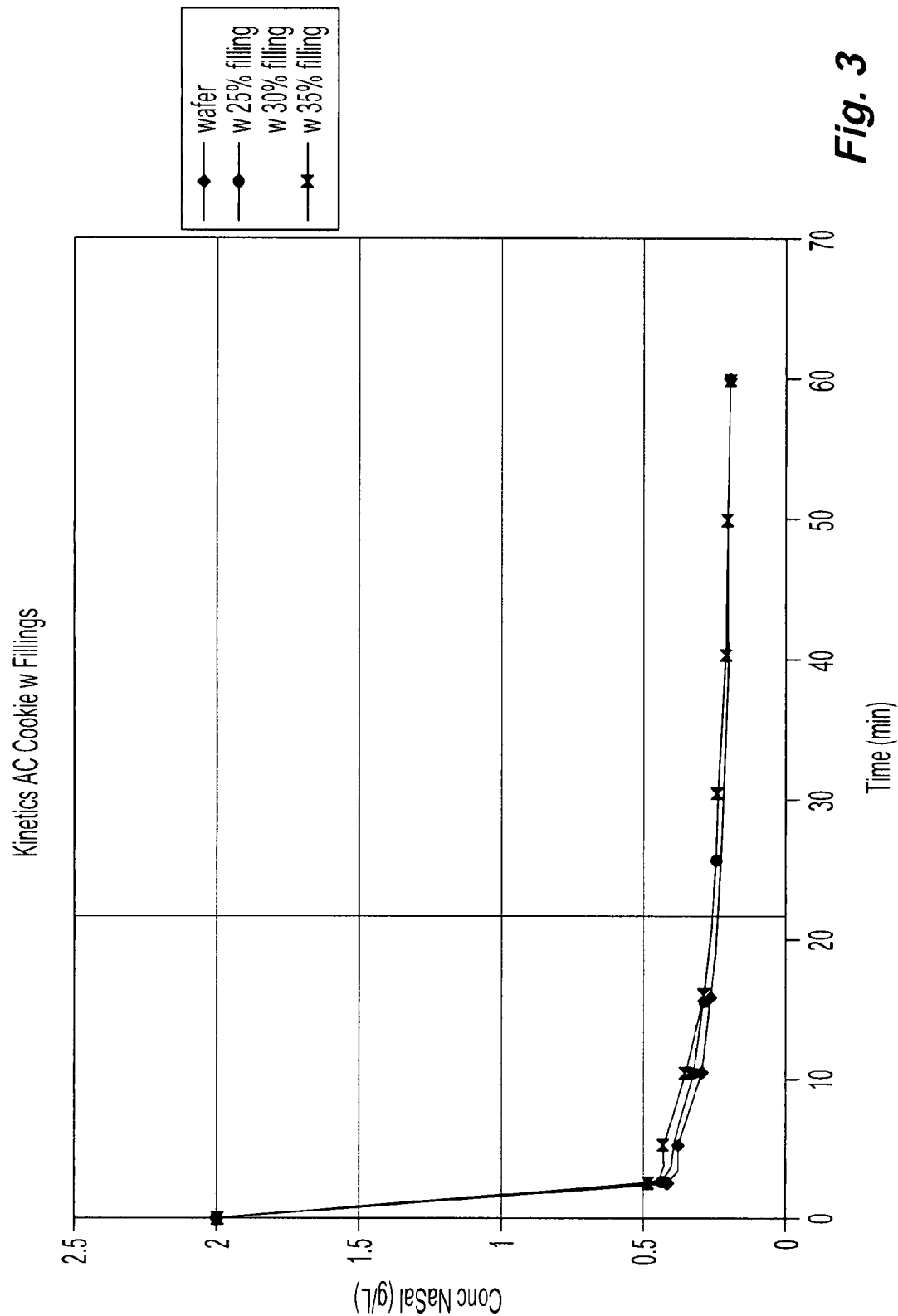
FIG. 3 illustrates the absorption of concentrated sodium salicylate in simulated gastric acid solution by an illustrative activated charcoal edible product of the invention with varying amounts of cream filling.
Figure 4:
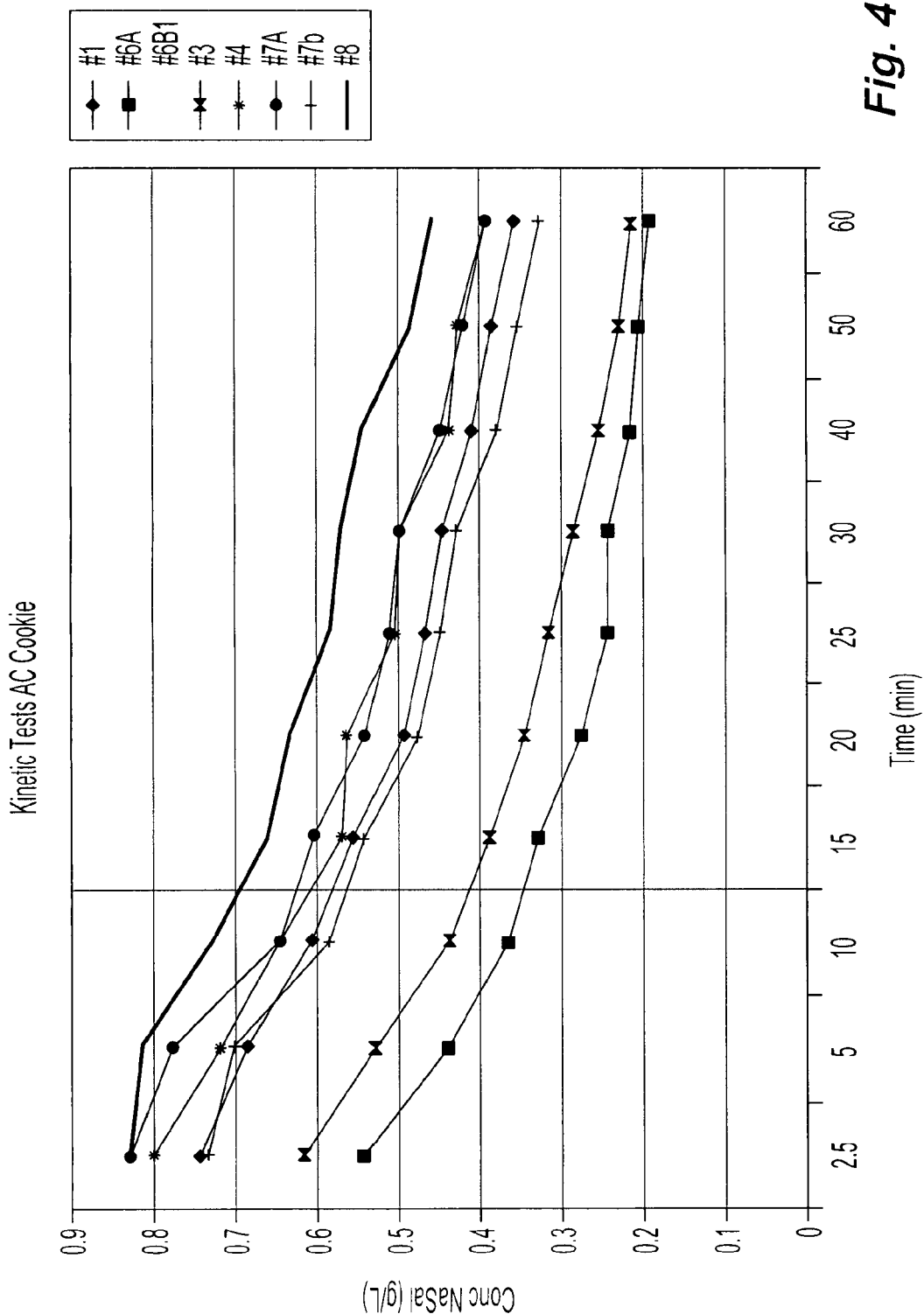
FIG. 4 illustrates the absorption of concentrated sodium salicylate in simulated gastric acid solution by illustrative 2.1 activated charcoal edible products of the invention of varying formulations.
Figure 5:
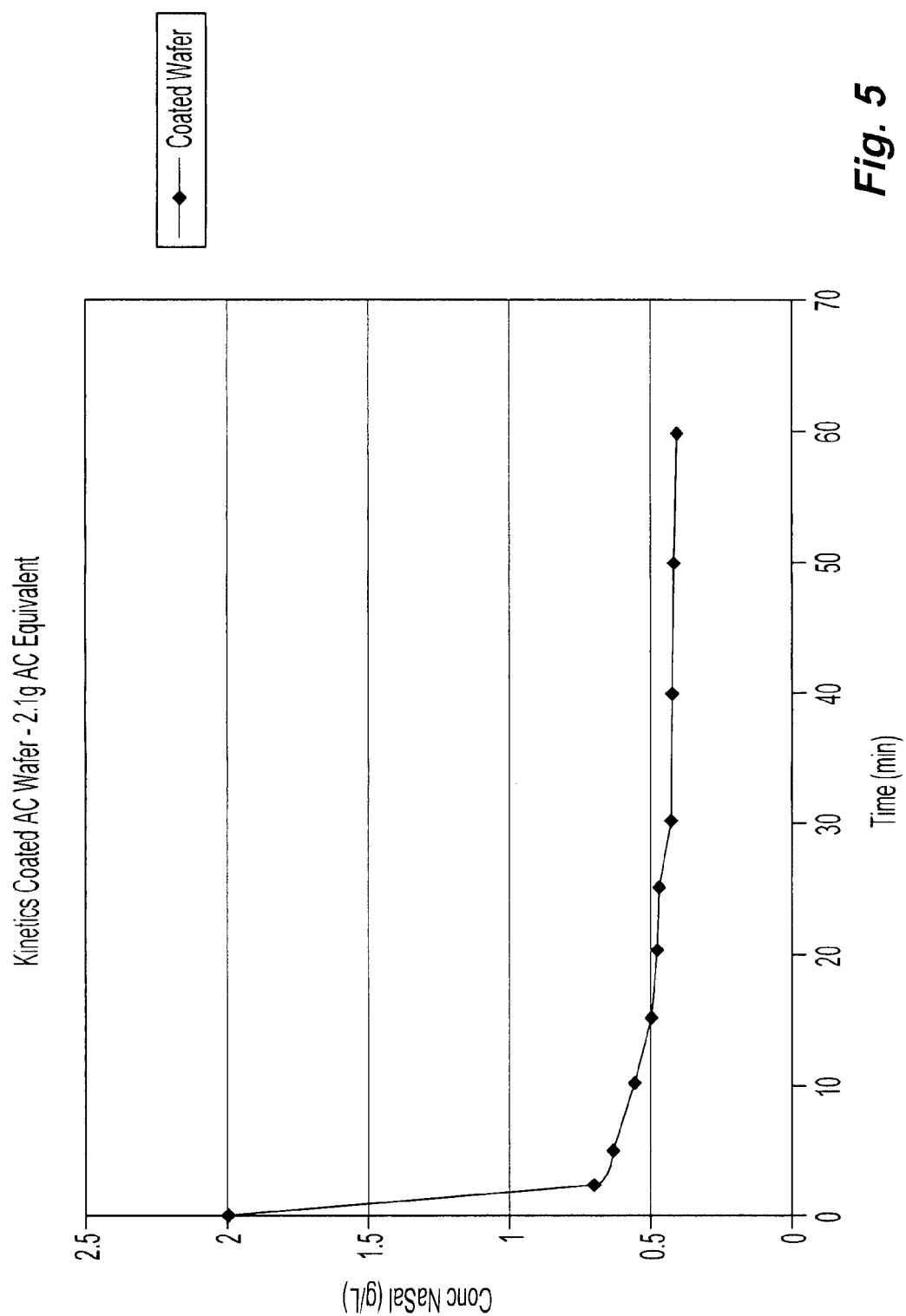
FIG. 5 illustrates the absorption of concentrated sodium salicylate in simulated gastric acid solution by an illustrative activated charcoal edible product of the invention containing 2.1 g activated charcoal.
Figure 6:
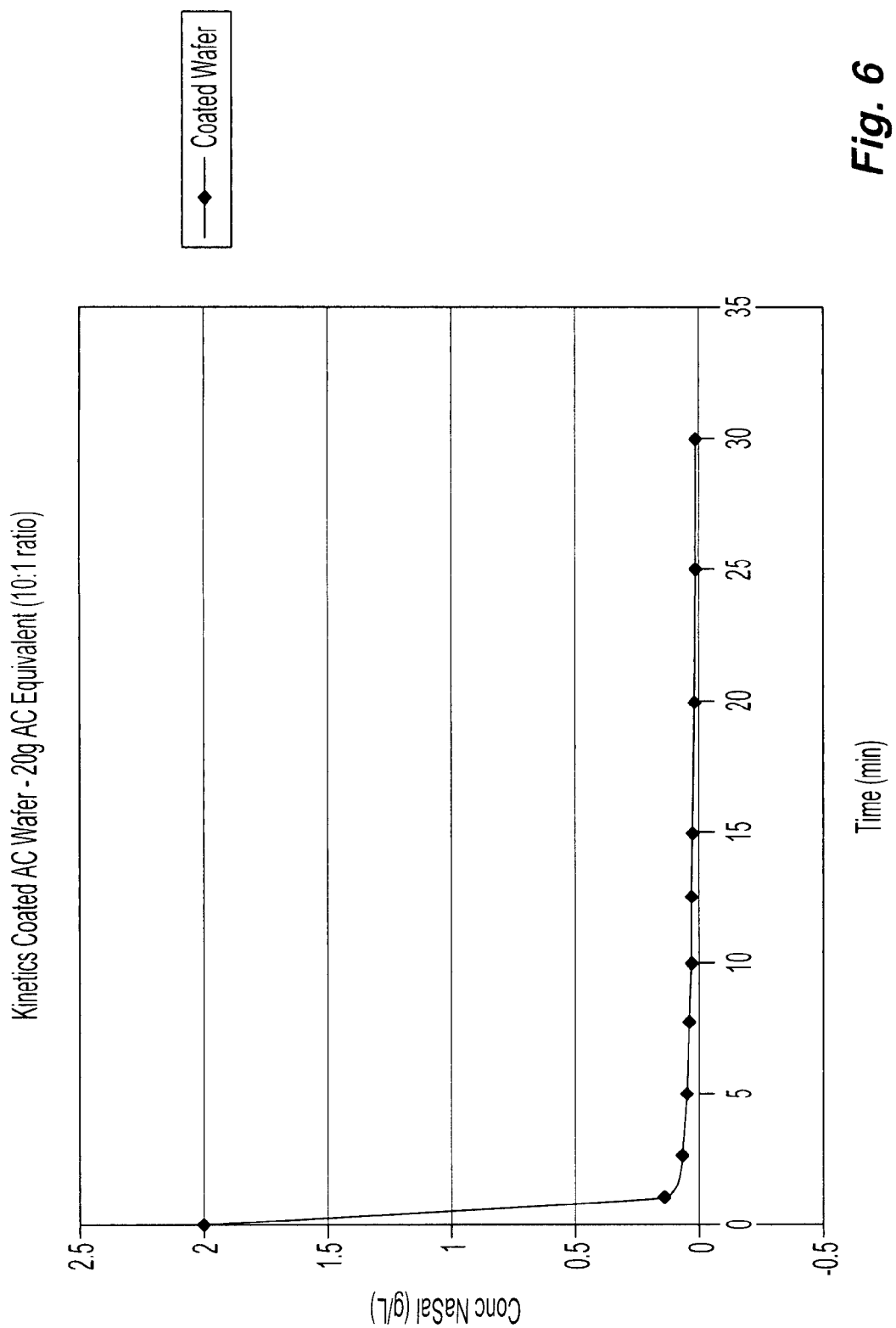
FIG. 6 illustrates the absorption of concentrated sodium salicylate in simulated gastric acid solution by illustrative activated charcoal edible product of the invention containing 20 g activated charcoal.

FIG. 3 illustrates comparative kinetic effects of varying amounts of filling on the adsorptivity of 2.1 g of activated charcoal. For this test, a cookie weighing approximately 6.80 grams (5.15 g wafers and 1.65 g filling) was crushed to simulate chewing, and then introduced into a given volume of the stock solution. This study illustrates the effect of adsorptivity on varying amounts of cream filling on the decontaminant and demonstrates no effect on adsorptivity of the activated charcoal.

Figure 1:
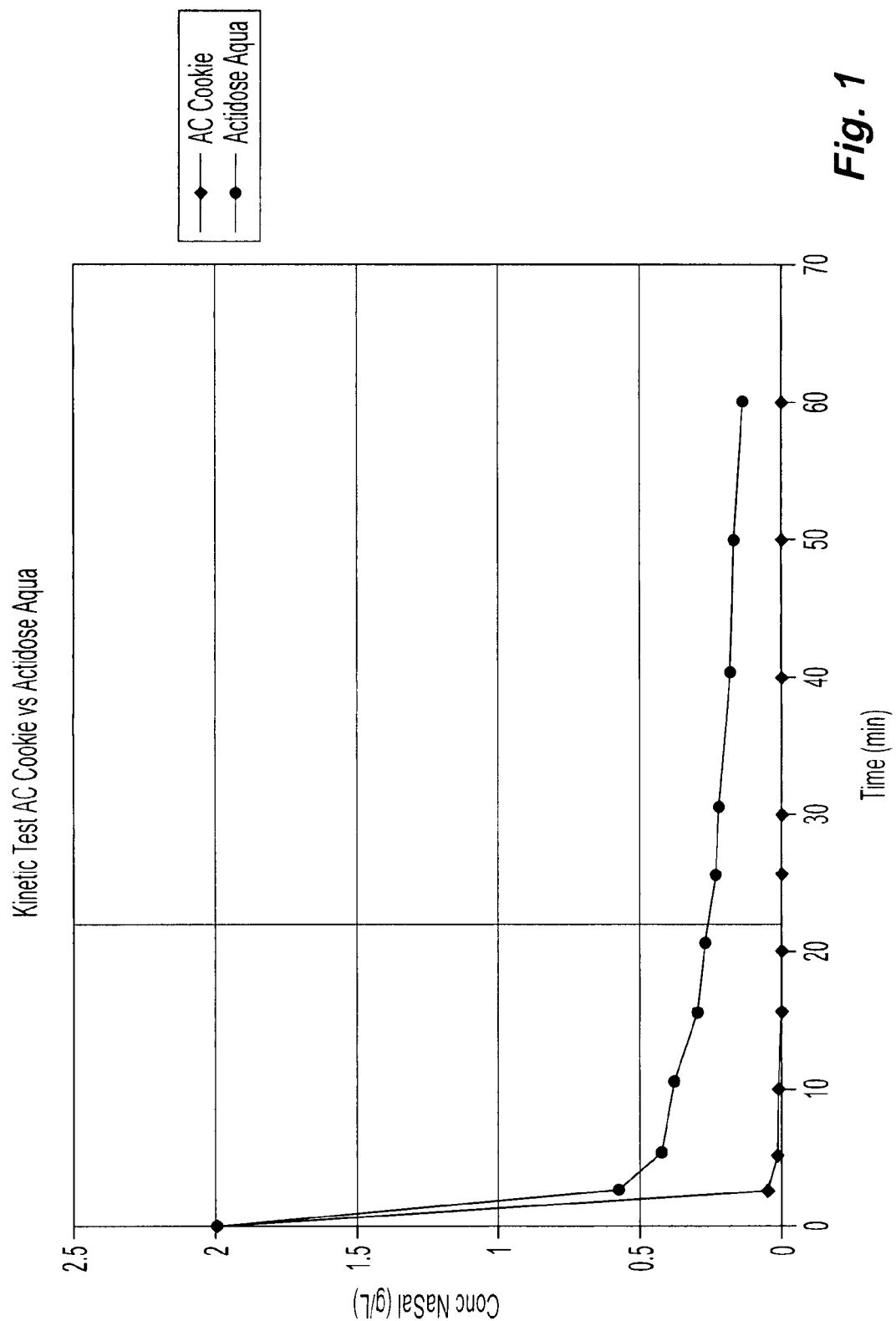
FIG. 1 illustrates the absorption of concentrated sodium salicylate in simulated gastric acid solution by an activated charcoal edible product containing 2.1 g activated charcoal as compared with ACTIDOSE AQUA containing the same amount of activated charcoal.
Figure 2:
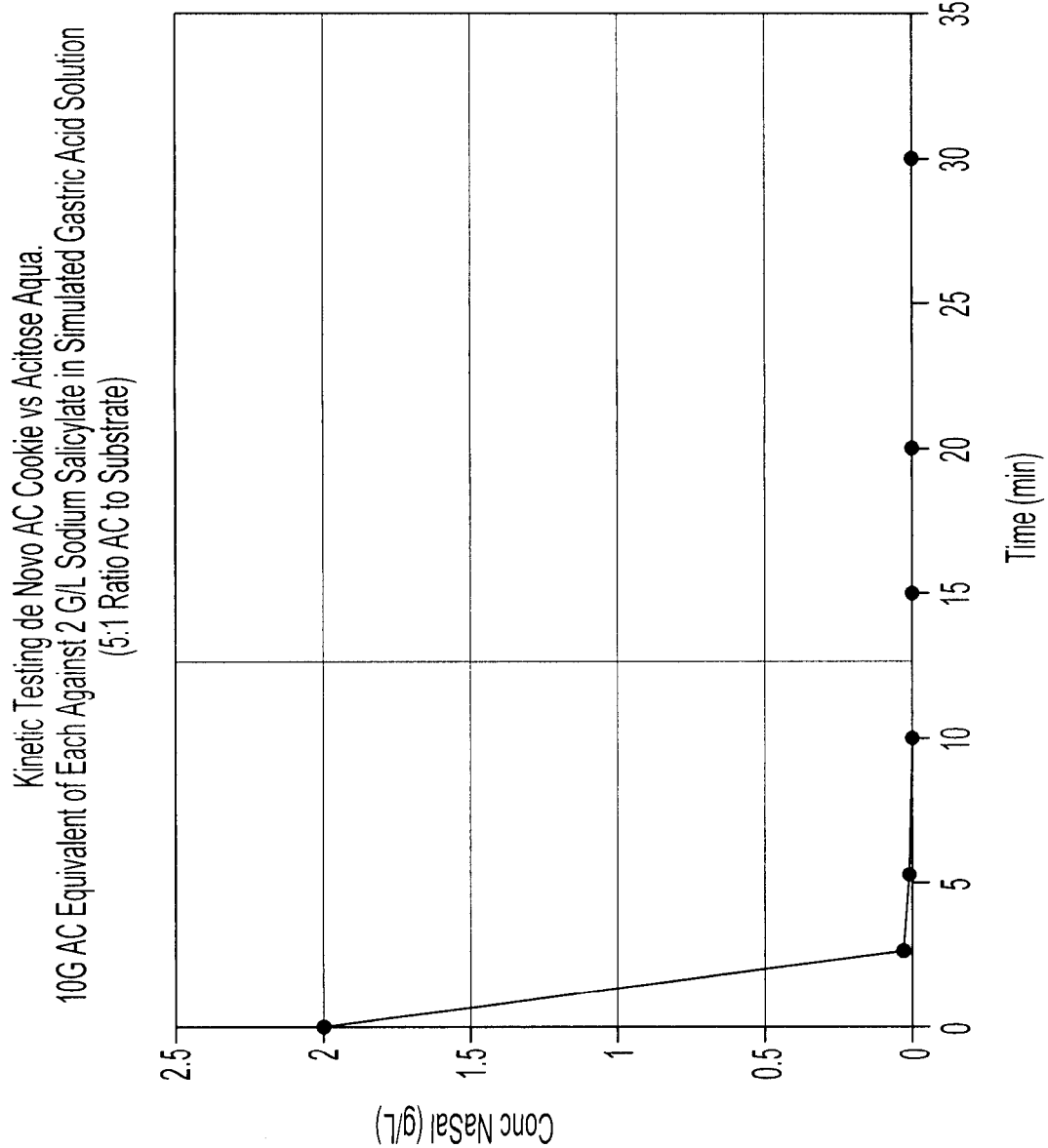
FIG. 2 illustrates the absorption of concentrated sodium salicylate in simulated gastric acid solution by an activated charcoal edible product containing 10 g activated charcoal as compared with ACTIDOSE AQUA containing the same amount of activated charcoal.

The superior adsorption performance of the subject decontaminant, edible product made in accordance with the inventive method is apparent from FIG. 2 when curve 1 is compared with curve 2, plotting the decrease in salicylate concentration upon introduction therein of 10.06 ml of ACTIDOSE AQUA, a liquid suspension commercially marketed by PADDOCK LABS, INC., Minneapolis, Minn. That amount of ACTIDOSE AQUA was determined to contain approximately the equivalent amount of activated charcoal as contained in the cookie sample from which curve 1 was derived. Comparison of the two curves indicates that the cookie produced by the instant inventive method not only reduced the salicylate concentration in the simulated gastric fluid solution at a significantly faster rate, but also yielded a significantly greater overall reduction in the concentration than a comparable amount of ACTIDOSE AQUA suspension. For instance, the salicylate concentration, 5 minutes subsequent to introduction of the subject cookie, was substantially below 0.2 g/L. Whereas, the salicylate concentration 5 minutes subsequent to introduction of the ACTIDOSE AQUA was observed to be approximately 0.5 g/L. After 30 minutes, the salicylate concentration had diminished to approximately 0.03 g/L with the subject cookie, whereas it had begun to level off at approximately 0.15 g/L with ACTIDOSE AQUA.

FIGS. 5-8 illustrate kinetic tests on illustrative edible decontaminant product of the invention. In one illustrative embodiment illustrated in FIGS. 5 and 7, 2.1 g of activated charcoal (essentially a 1:1 ratio with sodium salicylate) were added to illustrate the absolute degree to which the other ingredients interfere with activated charcoal. In another illustrative embodiment illustrated in FIGS. 6 and 8, 20 g of activated charcoal (essentially a 10:1 ratio with sodium salicylate) were added to illustrate how the product would perform in a clinical situation. FIGS. 7 and 8 further illustrate an illustrative embodiment of the invention in comparison with ACTIDOSE AQUA using 2.1 g and 20 g of activated charcoal, respectively.

7.2 Illustrative Embodiments of the Invention

Table 4 describes an illustrative embodiment of a mixture of ingredients of the edible product of the invention prior to baking.

TABLE 4

| Ingredient | Percent Weight %[1] |
|---|---|
| Neotame | 0.001% |
| Activated Charcoal | 24% |
| Cocoa | 1% |
| Salt | 0.2% |
| Rice Crisps | 11.14% |
| Sunnet Sweetner | 0.67% |
| Lecithin | 1.6% |
| Atmul | 3.55% |
| Emplex | 1.37% |
| Mix 3 minutes on low then add the following: | |
| Ammonia | 0.16% |
| Water | 53% |
| Glycerin | 6.05% |
| H.F. Corn Syrup | 27.09 |

[1]Weight percentages are determined prior to baking the ingredients.

In another illustrative embodiment of Table 4, the Sunnet Sweetener can be reduced or eliminated altogether and/or one or more flavoring agents, for example, chocolate flavoring or neotame may be added in a greater amount.

Table 5 describes another illustrative embodiment of a mixture of ingredients of the edible product of the invention prior to baking.

TABLE 5

| Ingredient | Preferred Weight %[1] | Weight % Range[1] |
|---|---|---|
| Activated Charcoal | 22% | 10-80% |
| Water | 31% | 0-80% |
| H.F. Corn Syrup | 19% | 0-55% |
| Rice Crisps | 8% | 0-50% |
| Glycerine | 3% | 0-10% |
| Flavor Bits/Inclusions | 17% | 0-35% |

[1]Weight percentages are determined prior to baking the ingredients.

Table 6 describes another illustrative embodiment of a mixture of ingredients of the edible product of the invention after baking.

TABLE 6

| Ingredient | Preferred Weight %[1] | Weight % Range[1] |
|---|---|---|
| Activated Charcoal | 34% | 10-80% |
| Water | 4% | 1-30% |
| H.F. Corn Syrup | 20% | 0-40% |
| Rice Crisps | 13% | 0-30% |
| Glycerine | 5% | 0-20% |
| Flavor Bits/Inclusions | 26% | 0-50% |

[1]Weight percentages are determined prior to baking the ingredients.

Table 7 below illustrates the adsorptivity of 2 g/L of NaSal using a 0.80 Cookie (2.1 g equivalent activated charcoal) and 7.7 cookies (20 g equivalent activated charcoal).

TABLE 7

| Time (min.) | Coated Wafer 0.8 Cookie (e.g., 2.1 g) Conc. | Time (min.) | Coated Wafer 7.7 Cookies (e.g., 20 g) Conc. |
|---|---|---|---|
| 2.5 | 0.701 | 1 | 0.129 |
| 5 | 0.636 | 2.5 | 0.060 |
| 10 | 0.559 | 5 | 0.040 |
| 15 | 0.512 | 7.5 | 0.032 |
| 20 | 0.486 | 10 | 0.024 |
| 25 | 0.471 | 12.5 | 0.023 |
| 30 | 0.435 | 15 | 0.023 |
| 40 | 0.435 | 20 | 0.019 |
| 50 | 0.425 | 25 | 0.017 |
| 60 | 0.412 | 30 | 0.017 |

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

What is claimed:

1. An edible, toxin-decontaminant product comprising a plurality of ingredients, said plurality comprising:
   A. a dry friable wafer in an amount of about 10 g and comprising about 2% water, which allows the wafer to maintain consistency without crumbling comprising;
      i. activated charcoal in an amount of 30% to 35% wt./wt.;
   B. at least one sweetener comprising: (N-[N-(3,3-dimethylbutyl)-L-a-aspartyl]-L-phenylalanine-1-methyl ester);
   C. ammonia, and
   D. an agent to improve porosity and texture.

2. The product of claim 1, wherein one or more of ingredients comprises a dough.

3. The product of claim 2, wherein the dough comprises one or more flavoring agents.

4. The product of claim 2, wherein the dough comprises one or more complexing or thickening agents or mixtures thereof.

5. The product of claim 2, wherein the dough comprises one or more emulsifying agents or mixtures thereof.

6. The product of claim 2, wherein the dough comprises an agent to improve porosity and texture.

7. The product of claim 1, further comprising a pharmaceutical agent, a homeopathic agent, or an herbal ingredient.

8. A gastrointestinal decontaminant product produced by the steps of:
   (a) combining a plurality of ingredients comprising:
      (i) one or more sweeting agents comprising: (N-[N-(3,3-dimethylbutyl)-L-α-aspartyl]-L-phenylalanine-1-methyl ester);
      (ii) activated charcoal;
      (iii) ammonia, and
      (iv) an agent to improve porosity and texture; and
      (v) dough;
   (b) blending the components to produce a mixture;
   (c) adding water to produce a mixture;
   (d) adding an agent to improve porosity and texture and blending; and
   (e) processing by heat to produce a first product; wherein the process results in an edible gastrointestinal decontaminant product comprising activated charcoal in an amount of 30% to 35% wt./wt. and a dry friable wafer in an amount of about 10 g and comprising about 2% water, which allows the wafer to maintain consistency without crumbling.

9. The product of claim 1, wherein said activated charcoal is characterized by an internal surface area of from about 800 $m^2/g$ to about 3,000 $m^2/g$.

10. The product of claim 1, wherein said activated charcoal is characterized by an internal surface area of about 2,000 $m^2/g$.

11. The product of claim 3, wherein the flavoring agent is vanilla flavor, chocolate flavor, salt, sugar, or a sweetener or mixtures thereof.

12. The product of claim 4, wherein the complexing or thickening agent is sodium stearoyl lactylate, high fructose corn syrup, or modified food starch or mixtures thereof.

13. The product of claim 5, wherein the emulsifying agent is a monoglyceride or diglyceride or mixtures thereof.

14. The product of claim 11, wherein the product includes the flavoring agent in the approximate weight range of about 0.001% to about 9% thereof.

15. An edible, toxin-decontaminant product comprising: (N-[N-(3,3-dimethylbutyl)-L-α-aspartyl]-phenylalanine-1-methyl ester), activated charcoal in an amount of about 70% wt./wt., cocoa, salt, rice crisps, lecithin, atmul, emplex, water, high fructose corn syrup, and optionally further comprising ammonia, glycerin, and sweetener.

\* \* \* \* \*